United States Patent [19]

Chen

[11] 4,263,393

[45] Apr. 21, 1981

[54] NOVEL ELECTRON DONOR PRECURSORS AND PHOTOGRAPHIC ELEMENT CONTAINING THEM

[75] Inventor: Chin H. Chen, Webster, N.Y.

[73] Assignee: Eastman Kodak Company, Rochester, N.Y.

[21] Appl. No.: 72,871

[22] Filed: Sep. 6, 1979

[51] Int. Cl.³ .......................... G03C 1/40; G03C 7/00; G03C 5/54; G03C 1/10

[52] U.S. Cl. .................................. 430/218; 430/222; 430/239; 430/241; 430/390; 430/440; 430/443; 430/446; 430/483; 430/564; 430/566; 430/559; 430/959

[58] Field of Search ............... 430/218, 222, 239, 241, 430/440, 443, 483, 959, 446, 390, 559, 566, 564

[56] References Cited

U.S. PATENT DOCUMENTS

| | | | |
|---|---|---|---|
| 2,957,883 | 10/1960 | Novello | 260/301 |
| 4,139,379 | 2/1979 | Chasman et al. | 430/222 |
| 4,139,389 | 2/1979 | Hinshaw et al. | 430/222 |

OTHER PUBLICATIONS

Hettler, *Advances in Heterocyclic Chemistry* vol. 15, Academic Press, N.Y., 1973, pp. 223-276.

*Primary Examiner*—Richard L. Schilling
*Attorney, Agent, or Firm*—Joshua G. Levitt

[57] ABSTRACT

Novel electron donor precursors have the structure:

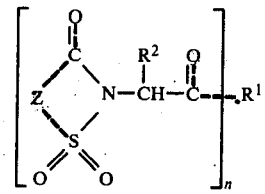

wherein:

Z represents the atoms to complete a mono-, bi- or tricyclic ring system, each ring of which contains 5 to 6 nuclear atoms;

n is 1 or 2;

$R^1$ is a monovalent aromatic group when n is 1 and a bivalent aromatic group when n is 2; and $R^2$ represents hydrogen, an alkyl group, an aryl group, an acyl group, an ester group or an amido group.

The compounds are useful in photographic elements, film units and processes to provide electrons to immobile compounds which must accept at least one electron before releasing a diffusible dye or photographic reagent.

37 Claims, No Drawings

NOVEL ELECTRON DONOR PRECURSORS AND PHOTOGRAPHIC ELEMENT CONTAINING THEM

This invention relates to new compounds, to photographic elements and film units, and to processes for forming image records in photographic elements. In one aspect this invention relates to novel electron donor precursors which can be incorporated in photographic elements and film units with immobile compounds which upon reduction under alkaline conditions undergo a reaction to release a diffusible dye or a photographic reagent.

It is known in the art to use various types of image dye-providing materials in photographic elements such as image transfer film units. Image dye-providing materials which are initially mobile in the film unit have been employed, for example, the mobile couplers and developers disclosed in U.S. Pat. No. 2,698,244, the mobile dyes and developers disclosed in U.S. Pat. No. 2,774,688 and the mobile preformed dyes disclosed in U.S. Pat. No. 2,983,606. Image dye-providing materials which are initially immobile have been employed, for example the materials disclosed in Canadian Pat. No. 602,607, U.S. Pat. Nos. 3,227,552, 3,628,952, 3,728,113, 3,725,062, 3,980,479, 4,076,529, 4,108,850, 4,139,379, 4,139,389 and U.S. Applications Ser. Nos. 534,966 filed Dec. 20, 1974 and 589,977 filed June 24, 1975. These image dye-providing materials include compounds which release dye in their oxidized form, of which the compounds disclosed in U.S. Pat. No. 4,076,529 are representative, and those which release dye in their reduced form, of which the compounds disclosed in U.S. Pat. Nos. 4,139,379 and 4,139,389 and representative.

The present invention relates to compounds useful with materials of the latter type, i.e., immobile materials which as incorporated in a photographic element or film unit are incapable of releasing a diffusible dye or photographic reagent, but during photographic processing under alkaline conditions are capable of accepting at least one electron (i.e. being reduced) and thereafter releasing a diffusible dye or photographic reagent. In particular, the present invention is directed to improved electron donor precursors useful with ballasted electron accepting nucleophilic displacement (BEND) compounds of the type described in U.S. Pat. Nos. 4,139,379 and 4,139,389.

BEND compounds are ballasted compounds that undergo intramolecular nucleophilic displacement to release a diffusible moiety. They contain a precursor for a nucleophilic group which accepts at least one electron before the compound can undergo intramolecular nucleophilic displacement. In a preferred embodiment described in U.S. Pat. No. 4,139,379 the BEND compounds are processed in silver halide photographic elements with an electron transfer agent and an electron donor (i.e., a reducing agent) which provides the necessary electrons to enable the compound to be reduced to a form which will undergo intramolecular nucleophilic displacement. In this embodiment the BEND compound reacts with the electron donor to provide a nucleophilic group which in turn enters into an intramolecular nucleophilic displacement reaction to displace a diffusible group from the compound, such as a diffusible dye or photographic reagent. However, where there are no electrons transferred to the electron-accepting nucleophilic precursor, it remains incapable of displacing the diffusible group. An imagewise distribution of electron donor is obtained in the photographic element by oxidizing the electron donor in an imagewise pattern before it has reacted with the BEND compound, leaving a distribution of unoxidized electron donor available to transfer electrons to the BEND compound. An imagewise distribution of oxidized electron donor is provided by reaction of the electron donor with an imagewise distribution of oxidized electron transfer agent, which in turn is obtained by reaction of a uniform distribution of electron transfer agent with an imagewise pattern of developable silver halide.

Thus, in processing an imagewise exposed photographic element containing a BEND compound the following reactions lead to an imagewise distribution of diffusible dye or photographic reagent: In exposed areas, developable silver halide is developed by electron transfer agent thereby providing oxidized electron transfer agent which reacts with and oxidizes electron donor thus preventing it from reacting with BEND compound. In unexposed areas, there is no developable silver halide and hence neither electron transfer agent nor electron donor are oxidized. Thus, electron donor reacts with BEND compound to release diffusible dye or photographic reagent.

In this embodiment pertinent reactions can be represented schematically as follows:

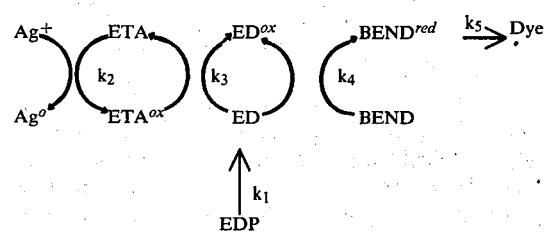

Half Cell Reactions

1. $Ag° \rightleftarrows Ag^+ + e^-$

2. $ETA \rightleftarrows ETA^{ox} + e^-$

3. $BEND^{red} \rightleftarrows BEND + e^-$

4. $ED \rightleftarrows ED^{ox} + e^-$ where:
$Ag^+$ is developable silver ion,
$Ag°$ is reduced silver,
ETA is electron transfer agent,
$ETA^{ox}$ is oxidized electron transfer agent,
BEND is as defined above,
$BEND^{red}$ is reduced BEND compound,
ED is electron donor compound,
$ED^{ox}$ is oxidized electron donor compound,
EDP is electron donor precursor and
Dye is released dye or photographic reagent.

For optimum results to be obtained it is desirable that there be a proper relationship between these various reactions, both with respect to relative halfwave potential and relative reaction rate. Thus, it is highly desirable that the halfwave potential of the halfcell reactions shown above increase in order of electronegativity from reaction 1 to reaction 4 (i.e., reaction 1 has the least negative reduction potential and reaction 4 has the most negative reduction potential). It is also highly desirable that the rate constant $k_3$ be much greater than the rate constant $k_4$ (i.e., the electron donor reacts much more rapidly with oxidized electron transfer agent than it does with BEND compound). If the rate constants were not in this order image discrimination would be poor since some release of dye could occur in areas where silver halide development was occurring. It is also desirable that the rate constants $k_1$ and $k_2$ be approximately equal, so that electron donor and oxidized electron transfer agent become available at about the same time and that the rate constant $k_3$ be about the same as, or slightly greater than, the rate constant $k_2$ so that there is no build up of excess electron donor. As will be appreciated, specific ranges of values which will apply in all cases cannot be assigned in view of the number of variables and the complex relations among them. U.S. Pat. No. 4,139,379 provides specific preferred ranges of values for relative reaction rates, referred to as redox t ½'s, and for halfwave potentials.

It have found a novel class of electron donor precursors which is highly useful in photographic elements containing an immobile material which must accept at least one electron (i.e., be reduced) before releasing a diffusible moiety. These electron donor precursors are highly active and therefore can lead to rapid release of the diffusible moiety. In particular, my precursors include compounds which are stable under keeping conditions yet under processing conditions rapidly unblock and make available an electron donor, thus leading to rapid release of the diffusible moiety.

In one aspect my invention relates to novel electron donor precursors.

In another aspect my invention relates to photographic elements comprising a support, a silver halide emulsion having associated therewith an immobile compound which upon reduction under alkaline conditions will release a diffusible dye or photographic reagent, and an electron donor precursor.

In yet another aspect my invention relates to an image transfer film unit comprising a photographic element having a support, a silver halide emulsion layer, and an immobile compound, as defined above, an image receiving layer, an alkaline processing composition contained within means from which it can be discharged within the film unit, an electron donor precursor and an electron transfer agent.

In still another aspect my invention relates to the process of preparing photographic images with photographic elements and image transfer film units as defined above.

Electron donor precursors of my invention can be represented by the structural formula:

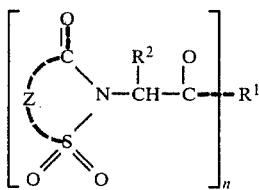

wherein:
Z represents the atoms to complete a mono-, bi- or tricyclic ring system, each ring of which contains 5 to 6 nuclear atoms;
n is 1 or 2;

$R^1$ is a monovalent aromatic group when n is 1 and a bivalent aromatic group when n is 2; and
$R^2$ represents hydrogen, an alkyl group, an aryl group, an acyl group, an ester group or an amido group.

The group represented by Z includes vinylene, phenylene and naphthylene groups which can be substituted with such groups as halogen (e.g., chloro, bromo, fluoro), amino, nitro, cyano, alkyl of 1 to 30 carbon atoms (e.g., methyl, ethyl, butyl, octyl, dodecyl, octadecyl, etc.), alkoxy of 1 to 30 carbon atoms (e.g. methoxy, butoxy, dodecyloxy, etc.), aryl of 6 to 30 carbon atoms (e.g. phenyl, naphthyl, biphenylyl, anthryl, etc.) aryloxy of 6 to 30 carbon atoms (e.g. phenoxy), acyl (e.g. $-COR^3$, $-SO_2R^3$, $-POR^3R^4$), ester (e.g, $-COOR^3$, $-SO_3R^3$, $-PO_2R^3R^4$, $-PO_3R^3R^4$) and amido e.g. sulfonamido ($-NR^3SO_2R^4$), carbonamido ($NR^3COR^4$), phosphoramido ($-NR^3POR^3R^4$), sulfamoyl ($-SO_2NR^3R^4$), carbamoyl ($-CONR^3R^4$) and phosphonyl diamide [$-PO(NR^3R^4)_2$] where $R^3$ and $R^4$ are each, individually, hydrogen, alkyl of 1 to 30 carbon atoms or aryl of 6 to 30 carbon atoms, provided that $R^3$ is hydrogen only if an $R^4$ group is present and that $R^3$ and $R^4$ are not both hydrogen, or together $R^3$ and $R^4$ can complete a 5- or 6-membered heterocyclic ring. The alkyl alkoxy, aryl and aryloxy substituents in Z and the $R^3$ and $R^4$ alkyl and aryl substituents can, in turn, be substituted with halogen, amino, nitro, cyano, carboxy, sulfo, hydroxy, alkyl, alkoxy, aryl, aryloxy, acyl, ester and amido groups as defined above.

The aromatic group represented by $R^1$ can be phenyl, phenylene, biphenylyl, biphenylylene, naphthyl, naphthylene, anthryl, anthrylene and the like, and can be substituted with such groups as halogen (e.g. fluoro, chloro, bromo), nitro, amino, cyano, alkyl of 1 to 30 carbon atoms, aryl of 6 to 30 carbon atoms, alkoxy of 1 to 30 carbon atoms, aryloxy of 6 to 30 carbon atoms, acyl (e.g. $-COR^3$, $-SO_2R^3$, $-POR^3R^4$), ester (e.g. $-COOR^3$, $-SO_3R^3$, $-PO_2R^3R^4$, $-PO_3R^3R^4$) and amido [e.g. $-NR^3SO_2R^4$, $-NR^3COR^4$, $-NR^3POR^3R^4$, $-SO_2NR^3R^4$, $-CONR^3R^4$, $-PO(NR^3R^4)_2$] where $R^3$ and $R^4$ are defined as above provided that sulfonamido, carbonamido or phosphoramido substituents are not in the 4-position of the aromatic group. The substituents on $R^1$ and the $R^3$ and $R^4$ alkyl and aryl substituents can, in turn, be substituted with halogen, nitro, amino, cyano, carboxy, sulfo, hydroxy, alkyl, alkoxy, aryl, aryloxy, acyl, ester and amido groups, as defined above.

The group represented by $R^2$ includes such groups as hydrogen, alkyl of 1 to 30 carbon atoms, aryl of 6 to 30 carbon atoms, acyl (e.g. $-COR^3$, $-SO_2R^3$,$POR^3R^4$), ester (e.g. $-COOR^3$, $-SO_3R^3$, $-PO_2R^3R^4$, $-POR^3R^4$) and amido [e.g. $-NR^3SO_2R^4$, $-NR^3COR^4$, $-NR^3POR^3R^4$, $-SO_2NR^3R^4$, $-CONR^3R^4$, $-PO(NR^3R^4)_2$] where $R^3$ and $R^4$ are as defined above. The alkyl and aryl group and the $R^3$ and $R^4$ alkyl and aryl substituents can be substituted with such groups as halogen, amino, nitro, cyano, carboxy, sulfo, hydroxy, alkyl, alkoxy, aryl, aryloxy, acyl, ester and amido, as defined above.

Preferred electron donor precursors of this invention are the N-phenacyl saccharins represented by the structural formula:

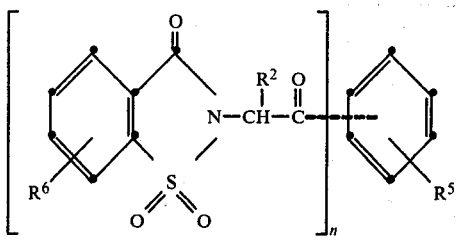

wherein:

$R^2$ and n are as defined above, $R^5$ is hydrogen or a substituent as defined above for substituents on $R^1$, and $R^6$ is hydrogen or a substituent as defined above for substituents on Z.

Preferably in structural formula II, n is 1;

$R^2$ is hydrogen or alkyl of 1 to 4 carbon atoms;

$R^5$ is hydrogen, halogen, nitro, alkyl of 1 to 30 carbon atoms, phenyl, or acyl, ester or amido as defined above provided that if $R^5$ is sulfonamido, carbonamido or phosphoramido it is in the ortho or meta position; and $R^6$ is hydrogen or acyl, ester or amido as defined above.

Particularly preferred are the electron donor precursors of structural formulae I and II where the various groups and substituents are so chosen that the compound is readily dispersible in aqueous coating compositions but is at least semi-immobile in the alkali-permeable layers of a photographic element or film unit. These criteria can be achieved if at least one of the substituents is an acyl, ester or amido group (preferably an amido group) and at least one of the substituents (which can be a substituent on the acyl, ester or amido group) is a long chain alkyl group (e.g. an alkyl group of 8 to 30 carbon atoms).

Specific representative electron donor precursors are shown below.

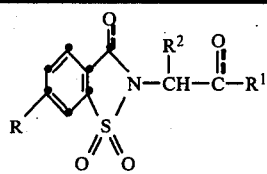

| Compound | $R^1$ | $R^2$ | R |
|---|---|---|---|
| 1 | Ph | H | H |
| 2 | Ph | Benzoyl | H |
| 3 | Ph | $CO_2Et$ | H |
| 4 | p-Nitrophenyl | H | H |
| 5 | Ph | Me | H |
| 6 | Anisyl | H | H |
| 7 | 4'-(Phenyl)phenyl | H | H |
| 8 | Ph | $\overset{O}{\underset{}{\|}}$ $-C-\overset{H}{N}-CH_2Ph$ | H |
| 9 | Ph | $-\overset{O}{\underset{}{\|}}C-Ph$ | H |
| 10 | Ph | $-\overset{O}{\underset{}{\|}}C-\overset{H}{N}C_{18}H_{37}$ | H |
| 11 | $-\langle O \rangle -\overset{H}{N}SO_2C_{16}H_{33}$ | $-\underset{O}{\overset{}{C}}-\overset{}{\underset{H}{N}}-\langle O \rangle -Cl$ | H |
| 12 | p-Fluorophenyl | H | H |
| 13 | m-Fluorosulfonylphenyl | H | H |
| 14 | p-(Methylsulfonyl)phenyl | H | H |
| 15 | $-\langle O \rangle -\overset{O}{\underset{\|}{C}}-CH_2-N\begin{pmatrix}\text{ring}\end{pmatrix}$ | H | H |
| 16 | Ph | Ph | H |
| 17 | $-\langle O \rangle -SO_2\overset{H}{N}C_{18}H_{37}$ | H | H |
| 18 | Ph | H | $NH_2$ |
| 19 | Ph | H | $-NHSO_2C_{16}H_{33}$ |
| 20 | $\langle O \rangle-\langle O \rangle$ | H | $NH_2$ |
| 21 | $\langle O \rangle-\langle O \rangle$ | H | $-N\overset{H}{\underset{}{}}\overset{O}{\underset{\|}{C}}-C_{17}H_{35}$ |
| 22 | Anisyl | H | $NH_2$ |

-continued

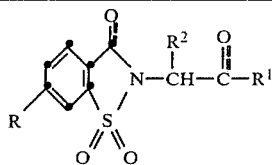

| Compound | R¹ | R² | R |
|---|---|---|---|
| 23 | Anisyl | H | H |
| | | | $-NSO_2C_{16}H_{33}$ |
| 24 | phenyl with H, $NSO_2C_{16}H_{33}$ | H | H |
| 25 | phenyl with Br, H, $SO_2NC_{18}H_{37}$ | H | H |
| 26 | phenyl with Br, $SO_2N(CH_3)$-propyl-$SO_2NC_{12}H_{25}$(H) | H | H |
| 27 | phenyl-$C(O)-N(CH_3)$-propyl-$SO_2NC_{12}H_{25}$(H) | H | H |
| 28 | phenyl-$SO_2N(CH_3)$-propyl-$SO_2NC_{12}H_{25}$(H) | H | H |
| 29 | phenyl-$NH_2$ | H | H |
| 30 | phenyl-$C(O)-N(CH_2\text{-})$-propyl-$SO_2N(H)$-phenyl($OC_{14}H_{29}$) | H | H |
| 31 | phenyl-$C(O)-N$-piperazine-$C(O)$-phenyl(H, $SO_2NC_{12}H_{25}$; H, $SO_2NC_{12}H_{25}$) | H | H |
| 32 | biphenyl | H | phenyl with H, $SO_2NC_{12}H_{25}$; $-NC(O)H$; H, $SO_2NC_{12}H_{25}$ |

The compounds of this invention can be prepared by condensation of the sodium salt of an appropriately substituted saccharin or homolog thereof with an appropriately substituted α-halo acetophenone according to the following reaction scheme:

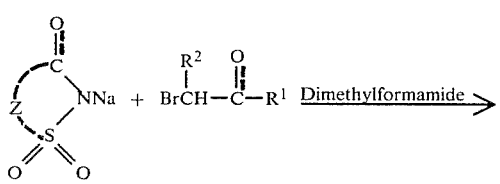

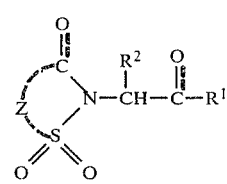

Preparation of specific compounds are shown in the examples.

While not wishing to be bound to a particular theory of operation, it is believed that the electron donating properties of these compounds are attributable to their cleaving under alkaline conditions to form an anion of an α-aminoenol group, according to the following reaction:

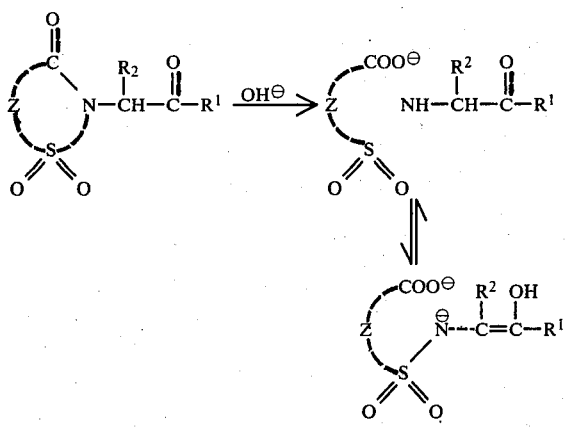

When employed with photographic elements and film units, the electron donor precursors of this invention can be incorporated in the processing composition with which the exposed element or film unit is contacted. (It will be noted that in the alkaline environment provided by the processing composition the electron donor precursor will be converted to an electron donor.) However, the electron donor precursor preferably is incorporated in the element or film unit in association with the immobile compound and most preferably is codispersed therewith in the same layer of the element or film unit. When incorporated in a photographic element or film unit the electron donor precursor is preferably semi-immobile and most preferably immobile in the alkali permeable layers of the element or film unit, so that the range of operation of the electron donor precursor is confined to the layer unit in which it is incorporated, thereby reducing or eliminating interimage contamination. A test for selecting electron donor precursors which are at least semi-immobile is given in above-mentioned U.S. Pat. No. 4,139,379 column 16, lines 11-34.

Preferred electron donor precursors yield, upon unblocking in 0.1 N sodium hydroxide, electron donors having a polarographic halfwave potential more negative than −300 mV with respect to a saturated calomel electrode. Particularly preferred are those electron donor precursors which yield, upon unblocking in 0.1 N sodium hydroxide, electron donors having a polarographic halfwave potential between −360 and −600 mV with respect to a saturated calomel electrode.

Further details regarding the use of electron donor precursors with photographic elements and film units are provided in the above-mentioned U.S. Pat. No. 4,139,379, the disclosure of which is incorporated herein by reference.

The electron donor precursors of this invention can be employed with any immobile compound which must accept at least one electron to release a diffusible dye or photographic reagent. Preferred such compounds are the ballasted electron-accepting nucleophilic displacement compounds (referred to herein by the acronym BEND compounds) described in the above-mentioned U.S. Pat. Nos. 4,139,379 and 4,139,389, the disclosures of which are incorporated herein by reference.

BEND compounds can generally be represented by the following schematic formula:

Ballasted    Electrophilic
(Carrier)$_x$(-Cleavage Group-)$_y$(-Diffusible Moiety)$_z$ where x, y and z are positive integers and preferably are 1 or 2; which includes compounds having more than one diffusible group attached to one ballast group or more than one ballast attached to one diffusible group; Ballasted Carrier is a group which is capable of rendering said compound immobile in alkali-permeable layers of a photographic element under alkaline processing conditions; and the Diffusible Moiety is a photographic reagent or an image dye-providing moiety; wherein said compound contains an Electrophilic Cleavage Group in each linkage connecting the ballasted carrier to the respective diffusible moiety, and one of the ballasted carriers or said diffusible moieties contains a group which, upon acceptance of at least one electron, provides a nucleophilic group capable of undergoing intramolecular nucleophilic displacement with said electrophilic cleavage group. Upon cleavage of the electrophilic cleavage group, part of the group will remain with the ballasted carrier and part of the group will remain with the diffusible moiety.

Preferred BEND compounds can be represented by the structural formula:

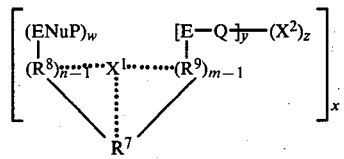

wherein:
w, x, y, z, n and m are positive integers of 1 or 2;
ENuP is an electron-accepting nucleophilic precursor group;
$R^7$ is a cyclic organic group to which ENuP and E are attached;
$R^8$ and $R^9$ are bivalent organic groups containing from 1 to 3 atoms in the bivalent linkage;
E and Q provide an electrophilic cleavage group where
  E is an electrophilic group and
  Q is a bivalent amino group, oxygen atom, selenium atom or sulfur atom providing a mono-atom linkage between E and $X^2$ and which is displaceable from E by the nucleophilic group provided by ENuP;
$X^1$ is a substituent on at least one of $R^7$, $R^8$ and $R^9$; and
one of $X^1$ or Q—$X^2$ is a ballasting group of sufficient size to render said compound immobile in an alkali-permeable layer of a photographic element, and one of $X^1$ and Q—$X^2$ is a diffusible image dye-providing material or a diffusible photographic reagent.

The electron-accepting nucleophilic group precursor represented by ENuP can be a precursor for a hydroxylamino group such as a nitroso group (NO), a stable nitroxyl free radical (N—O·), or, preferably, a nitro group (NO$_2$), or it can be a precursor for a hydroxy group such as an oxo group (=O), or an imine group which is hydrolyzed to an oxo group in an alkaline environment.

The cyclic organic group represented by $R^7$ includes bridged-ring groups, polycyclic groups and the like, which preferably have from 5–7 members in the ring to which ENuP and E are attached. $R^7$ is preferably an aromatic ring having 5–6 members in the ring and is a carbocyclic ring, e.g., benzenoid groups, etc., or is a heterocyclic ring including nonaromatic rings where ENuP is part of the ring, (e.g., where ENuP is a nitroxyl group with the nitrogen atom in the ring.) Generally, $R^7$ contains less than 50 atoms and preferably less than 15 atoms.

The bivalent organic groups containing from 1–3 atoms in the bivalent linkage represented by $R^8$ and $R^9$ be alkylene, oxaalkylene, thiaalkylene, azaalkylene, alkyl- or aryl-substituted nitrogen and the like, including large groups in side chains on said linkage which can function as a ballast, e.g., groups containing at least 8 carbon atoms and which groups can be $X^1$ when $X^1$ is a ballast group. In certain embodiments $R^9$ preferably contains a dialkyl-substituted methylene linkage such as a dimethylalkylene which is especially useful when Q is an oxygen atom and $R^1$ and ENuP form a quinone.

In the electrophilic cleavage group provided by E and Q, E is preferably a carbonyl group, including carbonyl (—CO—) and thiocarbonyl (—CS—) or it can be a sulfonyl group. The mono atom linkage provided by Q is preferably a nitrogen atom which provides a bivalent amino group. The third valence of this nitrogen atom can be satisfied with a hydrogen atom, an alkyl group containing from 1–20 atoms and preferably 1–10 carbon atoms, including substituted carbon atoms and carbocyclic group, an aryl group containing from 6–20 carbon atoms including substituted aryl groups or a group which is connected to $X^2$ to form a 5- to 7-atom cyclic group.

The groups represented by $R^7$, $R^8$, and $R^9$ are selected to provide substantial proximity of ENuP to E so as to permit intramolecular nucleophilic cleavage of Q from E and are preferably selected to provide 1 or 3 to 5 atoms between the atom which is the nucleophilic center of the nucleophilic group and the atom which is the electrophilic center, whereby said compound is capable of forming a 3- or 5- to 7-membered ring and most preferably a 5- or 6-membered ring upon intramolecular nucleophilic displacement of the group $Q-X^2$ from said electrophillic group.

The dye-providing material provided by $X^1$ or $Q-X^2$ is preferably a preformed dye or a shifted dye. Dyes of this type are well known in the art and include dyes such as azo dyes including metalizable azo dyes and metalized azo dyes, azomethine (imine) dyes, anthraquinone dyes, alizarin dyes, merocyanine dyes, quinoline dyes, cyanine dyes and the like. The shifted dyes include those compounds wherein the light-absorption characteristics are shifted hypsochromically or bathochromically when subjected to a different environment such as a change in pH, reaction with a material to form a complex such as with a metal ion, removal of a group such as a hydrolyzable acyl group connected to an atom of the chromophore. In certain embodiments, the dye-providing material is a chelating dye moiety that upon release can diffuse to an image-receiving layer containing metal ions to form a metal-complexed dye.

In certain preferred embodiments, the cleavable group is used as a substituent on a shiftable dye to control the resonance of the dye. Upon release of the dye, it will undergo a bathochromic or hypsochromic shift. In this embodiment, any dye can be used which contains an ionizable nitrogen atom, oxygen atom, sulfur atom or selenium atom which affects the resonance of the dye. The dye is attached to the compound so that the ionizable group is the leaving group in the electrophilic cleavage group.

In another embodiment, the dye providing material is an image-dye precursor. The term "image-dye precursor" is understood to refer to those compounds that undergo reactions encountered in a photographic imaging system to produce an image dye, such as color couplers, oxichromic compounds, and the like.

The photographic reagent moiety represented by $X^1$ or $Q-X^2$ can be a silver complexing agent, a silver halide solvent, a fixing agent, a toner, a hardener, an antifoggant, a fogging agent, a sensitizer, a desensitizer, a developer or an oxidizing agent. In other words, $X^1$ and $Q-X^2$ can represent any moiety, which in combination with a hydrogen atom, provides a photographic reagent upon cleavage. Where the photographic reagent is a development inhibitor or an antifoggant, Q is preferably an active nitrogen atom or an active sulfur atom, such as in a benzotriazole, benzimidazole or a mercaptotetrazole where the compound is blocked prior to release and becomes active upon release.

The nature of the ballasting groups in the above compounds is not critical as long as the portion of the compound on the ballast side of E is primarily responsible for the immobility; the other portion of the molecule on the remaining side of E generally contains sufficient solubilizing groups to render it mobile and diffusible in an alkaline medium after cleavage. Thus, $X^1$ could be a relatively small group if the remainder of $R^7$, $R^8$ and $R^9$ confers sufficient insolubility to the compound to render it immobile. However, when $X^1$ or $—X^2$ serve as the ballast function, they generally comprise long-chain alkyl radicals, as well as aromatic radicals of the benzene and naphthalene series. Typical useful groups for the ballast function contain at least 8 carbon atoms and preferably at least 14 carbon atoms. Where $X^1$ is a ballast, it can be one or more groups substituted on $R^7$, $R^8$, or $R^9$ which confer the desired immobility. Thus, for example, two small groups, such as groups containing from 5–12 carbon atoms, can be used to achieve the same immobility as one long ballast group containing from 8–20 carbon atoms. Where multiple ballast groups are used, it is sometimes convenient to have an electron-withdrawing group linkage between the major part of the ballast group and an aromatic ring to which it is attached, especially when the electron-accepting nucleophilic precursor is a nitro substituent on said ring.

The term "nucleophilic group" as used herein refers to an atom or group of atoms that have an electron pair capable of forming a covalent bond. Groups of this type are sometimes ionizable groups that react as anionic groups. The term "electron-accepting nucleophilic precursor group" refers to that precursor group that, upon accepting at least one electron, i.e., in a reduction reaction, provides a nucleophilic group. The electron-accepting nucleophilic precursor groups are less nucleophilic in character than the reduced group or have a structure that adversely affects the proximity of the nucleophilic center with respect to the electrophilic center.

The nucleophilic group can contain only one nucleophilic center such as the oxygen atom in a hydroxy group, or it can contain more than one atom which can be the nucleophilic center such as in the case of a hydroxylamino group where either the nitrogen atom or the oxygen atom can be the nucleophilic center. Where more than one nucleophilic center is present in the nucleophilic group on the intramolecular nucleophilic displacement compounds of this invention, the nucleophilic attack and displacement will generally occur through the center which is capable of forming the most favored ring structure; i.e., if the oxygen atom of the hydroxylamino group would form a 7-membered ring and the nitrogen atom would form a 6-membered ring, the active nucleophilic center would generally be the nitrogen atom.

The term "electrophilic group" refers to an atom or group of atoms that are capable of accepting an electron pair to form a covalent bond. Typical electrophilic groups are sulfonyl groups (—$SO_2$—), carbonyl (—CO—) and thiocarbonyl (—CS—) and the like, where the carbon atom of the carbonyl group forms the electrophilic center of the group and can sustain a partial positive charge. The term "electrophilic cleavage group" is used herein to refer to a group (—E—Q—) wherein E is an electrophilic group and Q is a leaving group providing a mono atom linkage between E and $X^2$. The leaving group is capable of accepting a pair of electrons upon being released from the electrophilic group.

In certain embodiments, the BEND compounds useful in accordance with the invention are ballasted compounds having the structure:

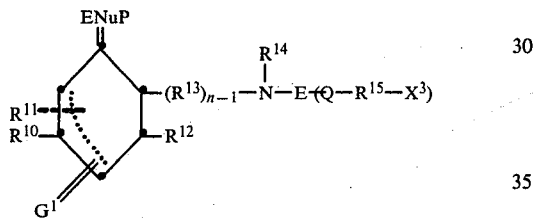

wherein ENuP is an electron-accepting nucleophilic precursor for a hydroxy nucleophilic group including imino groups and preferably oxo groups;

$G^1$ is an imino group including alkylimino groups and sulfonimido groups, a cyclic group formed with $R^{10}$ or $R^{12}$ or any of the groups specified for ENuP, and preferably $G^1$ is para to the ENuP group;

E is an electrophilic group which can be carbonyl —CO— or thiocarbonyl —CS— and is preferably carbonyl;

Q is a bivalent amino group, an oxygen atom, a sulfur atom or a selenium atom providing a mono atom linkage between E and $R^{15}$ and when it is a trivalent atom it can be monosubstituted with a hydrogen atom, an alkyl group containing from 1–10 carbon atoms including substituted alkyl groups, aromatic groups containing 5–20 carbon atoms including aryl groups and substituted aryl groups and groups which are connected to $R^{15}$ to form a 5- to 7-atom cyclic group;

$R^{13}$ is an alkylene group containing from 1–3 carbon atoms in the linkage including substituted alkylene groups and preferably is an alkylene group containing 1 carbon atom in the bivalent linkage such as a methylene linkage or a dialkyl- or diaryl-substituted methylene linkage;

n is an integer of 1 or 2;

$R^{15}$ can be an aromatic group containing at least 5 atoms and preferably from 5–20 atoms including heterocyclic groups, for example, groups containing a nucleus such as pyridine, tetrazole, benzimidazole, benzotetrazole, isoquinoline and the like, or a carbocyclic arylene group which preferably contains from 6–20 carbon atoms and which is preferably a phenylene group or a naphthylene group including substituted phenylene and naphthylene groups, or $R^{15}$ can be an aliphatic hydrocarbon group such as an alkylene group containing from 1–12 carbon atoms, including substituted alkylene groups and the like;

$R^{14}$ can be an alkyl group containing from 1–40 carbon atoms, including substituted alkyl groups and cycloalkyl groups, an aryl group containing from 6–40 carbon atoms, including substituted aryl groups and the like, or it can be the substituent $X^1$;

$R^{12}$, $R^{10}$ and $R^{11}$ can each be mono atom substituents such as hydrogen or halogen atoms or preferably poly atom substituents such as an alkyl group containing from 1–40 carbon atoms, including substituted alkyl groups and cycloalkyl groups, an alkoxy group, an aryl group containing from 6–40 carbon atoms, including substituted aryl groups, a carbonyl group, a sulfamyl group, a sulfonamido group and the like, or they can each be the substituent $X^1$ with the provision that $R^{12}$ and $R^{11}$ or $R^{10}$ and $R^{11}$, when they are on adjacent positions of the ring, may be taken together to form a 5- to 7-membered ring with the remainder of the molecule including bridged rings and the like, and with the provision that, when $R^{15}$ is an aliphatic hydrocarbon group such as an alkylene group, $R^{12}$ and $R^{10}$ must be poly atom substituents, and preferably $R^{11}$ is a poly atom substituent, and when $G^1$ is an electron-accepting nucleophilic precursor group as defined for ENuP, the $R^{10}$ or $R^{12}$ substituent adjacent $G^1$ can be the group:

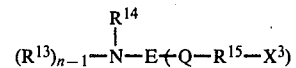

to provide a compound which has multiple groups which can be released by nucleophilic displacement;

$X^1$ is provided in at least one of the substituted positions and each of $X^1$ and —(Q—$R^{15}$—$X^3$) can be a ballasting group of sufficient size to render said compound immobile in an alkali-permeable layer of a photographic element, or a photographically useful moiety, provides one of $X^1$ and —(Q—$R^{15}$—$X^3$) is a ballast group and the other is a photographically useful moiety, such as a photographic reagent, or a dyeproviding material; and $R^{13}$ is selected to provide substantial proximity of the nucleophilic group to E to permit intramolecular nucleophilic cleavage of Q from E, and is preferably selected to provide 3–5 atoms between the atom which is the nucleophilic center of said nucleophilic group and the atom which is the electrophilic center of said electrophilic group, whereby said compound is capable of forming a 5- to 8-membered ring and most preferably a 5- or 6-membered ring upon intramolecular nucleophilic displacement of the group —(Q—$R^{15}$—$X^3$) from said electrophilic group.

In certain embodiments, the BEND compounds useful in this invention are compounds which have the formula:

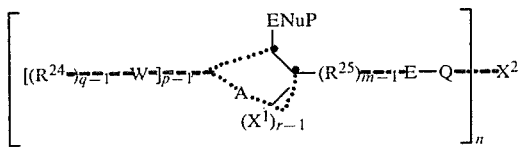

where:

ENuP is an electron-accepting precursor for a hydroxylamino group such as nitroso (NO), stable nitroxyl radicals and preferably nitro groups ($NO_2$);

A represents a group containing the atoms necessary to form a 5- or 6-membered aromatic ring with the remainder of said formula, including polycyclic aromatic-ring structures, and wherein the aromatic rings can be carbocyclic rings or heterocyclic rings such as groups containing aromatic onium groups in the ring, and A preferably represents the groups necessary to form a carbocyclic ring system such as a benzene ring, a naphthalene ring, etc.;

W is an electron-withdrawing group having a positive Hammett sigma value and includes groups such as cyano, nitro, fluoro, chloro, bromo, iodo, trifluoromethyl, trialkyl ammonium, carbonyl, N-substituted carbamoyl, sulfoxide, sulfonyl, N-substituted sulfamoyl, ester and the like;

$R^{24}$ is a hydrogen atom, a substituted or unsubstituted alkyl group containing from 1-30 carbon atoms, or a substituted or unsubstituted aryl group containing from 6-30 carbon atoms;

$R^{25}$ is a bivalent organic group containing from 1-3 atoms in the bivalent linkage and can be alkylene groups, oxaalkylene, thioalkylene, iminoalkylene, alkyl or arylsubstituted nitrogen and the like and is preferably an alkylene linkage containing at least one dialkyl- or diarylsubstituted methylene in said linkage;

m and q are positive integers of 1 or 2;

p and r are positive integers of 1 or greater and preferably p is 3-4, with $[(R^{24})_{\overline{q-1}}W]$ being a substituent on any portion of the aromatic-ring structure of A;

E and Q provide an electrophilic cleavage group where E is an electrophilic center and is preferably a carbonyl group including carbonyl (—CO—) and thiocarbonyl (—CS—) or it can be a sulfonyl group and Q is a group providing a monoatom linkage between E and $X^2$ wherein said monoatom can be an oxygen atom, a sulfur atom, a selenium atom, a nitrogen atom which provides an amino group and the like, and preferably Q is an amino group with an alkyl group substituent containing from 1-20 atoms, including substituted alkyl groups or groups which are connected to $X^2$ to form cyclic groups such as piperidine groups and the like;

n is an integer of 1-3 and is preferably 1;

$X^2$, together with Q, is either an image dye-providing material, an image-dye precursor or a photographic reagent;

$X^1$ is a ballasting group and preferably is a substituted or unsubstituted alkyl group containing from 8-30 carbon atoms, a substituted or unsubstituted aryl group containing from 8-30 carbon atoms and the like, including the necessary linking groups to the aromatic ring, with the provision that at least one of $X^1$ or $R^{24}$ is present in said compound and is a group of sufficient size to render said BEND compound immobile and nondiffusible in the alkali-permeable layers of a photographic element, i.e., preferably at least one of $X^1$ or $R^{24}$ contains from 12-30 carbon atoms.

It is to be understood that, when multiple groups are present in the compound as designated in the above formula, they may be identical or different; i.e., when p is 3, each $(R^{24}-W)$ may be selected from different substitutents as specified.

The electron-withdrawing groups referred to for the compounds of the above formulae generally are those groups which have a positive Hammett sigma value and preferably a sigma value more positive than 0.2 or a combined effect of more than 0.5 as substituents of the aromatic ring. The Hammett sigma values are calculated in accordance with the procedures in *Steric Effects in Organic Chemistry*, John Wiley and Sons, Inc., 1956, pp. 570-574, and *Progress in Physical Organic Chemistry*, Vol. 2, Interscience Publishers, 1964, pp. 333-339.

Typical useful electron-withdrawing groups having positive Hammett sigma values include cyano, nitro, fluoro, bromo, iodo, trifluoromethyl, trialkylammonium, carbonyl, N-substituted carbamoyl, sulfoxide, sulfonyl, N-substituted sulfamoyl esters and the like. Where the term "aromatic ring having an electron-withdrawing substituent" is used herein, it refers to onium groups in the ring and to those groups substituted directly on the ring which may be linkage for other groups such as ballast groups.

In another preferred embodiment of this invention, the BEND compounds have the formula:

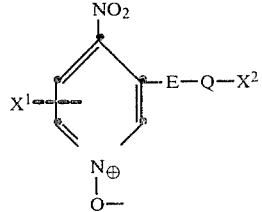

where:

E, Q, $X^1$ and $X^2$ are as defined above.

Typical useful BEND compounds are as follows:

BEND-1
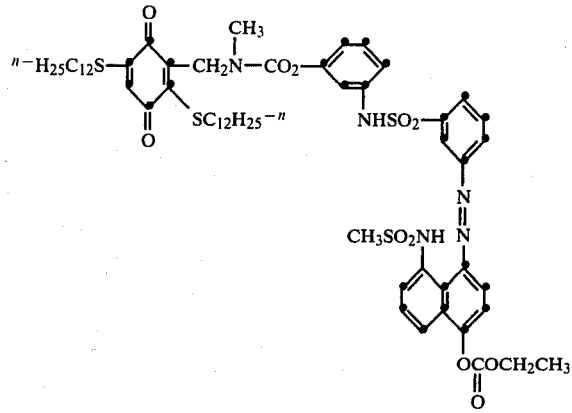
BEND-2
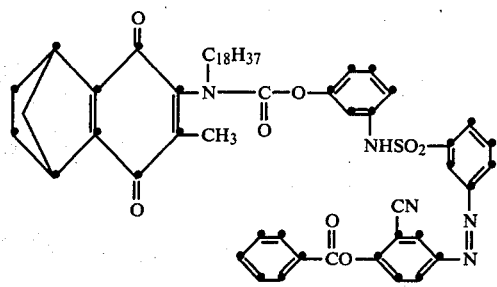
BEND-3
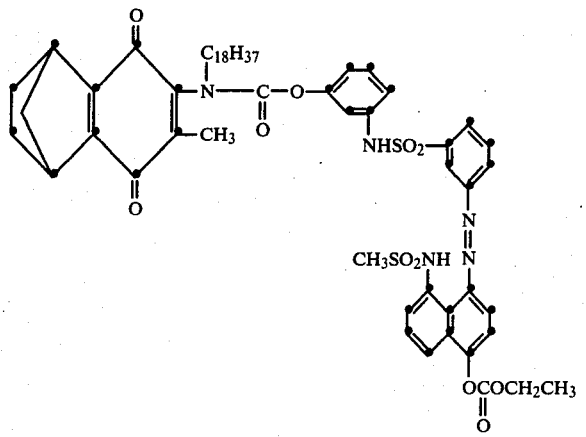
BEND-4
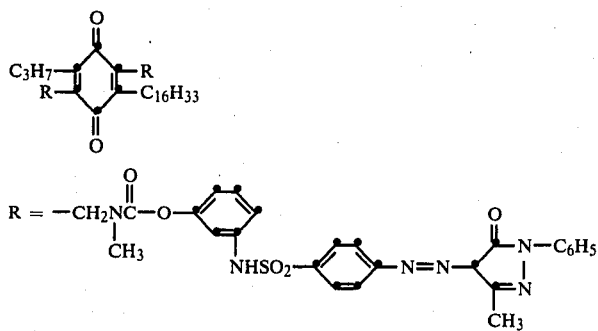
BEND-5
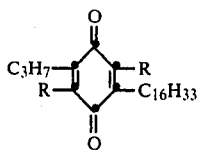

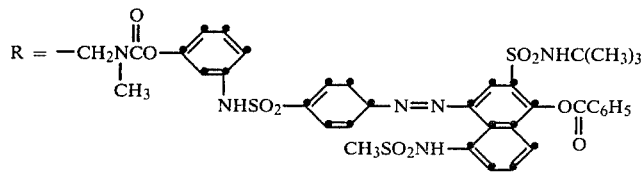
BEND-6
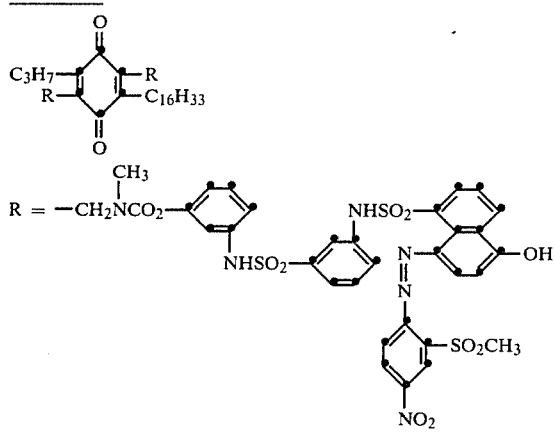
BEND-7
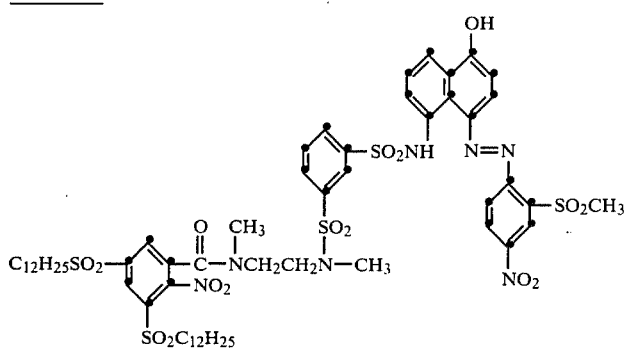
BEND-8
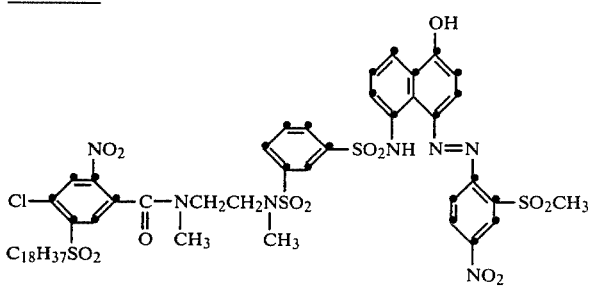
BEND-9
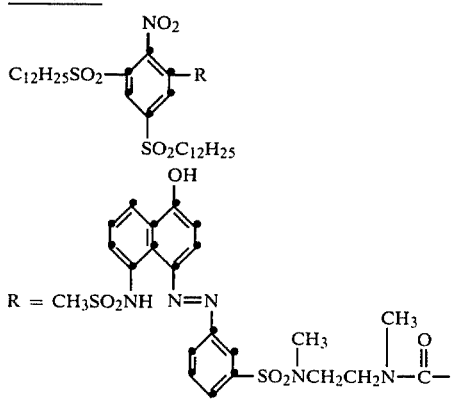
BEND-10

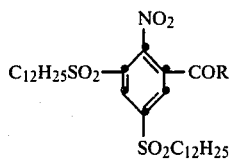
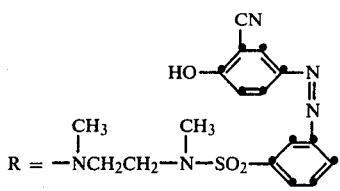
BEND-11
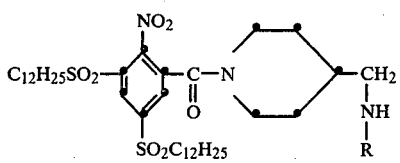
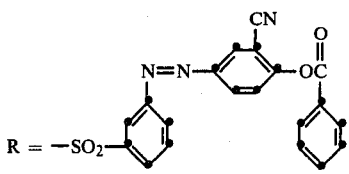
BEND-12
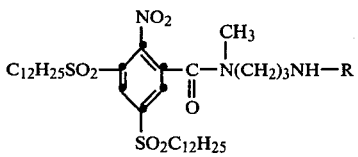
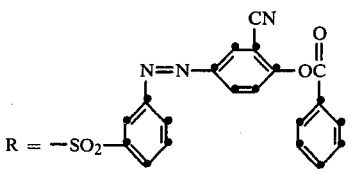
BEND-13
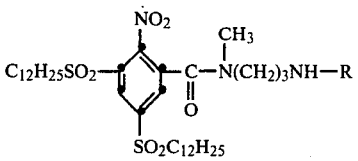
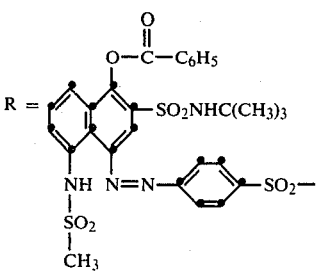
BEND-14

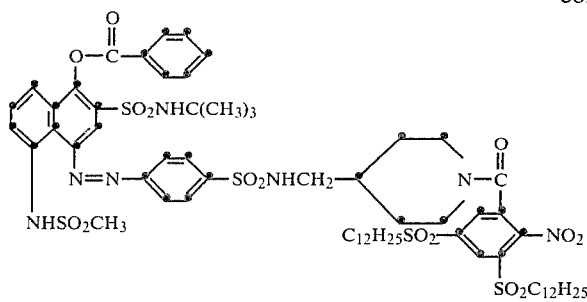
BEND-15
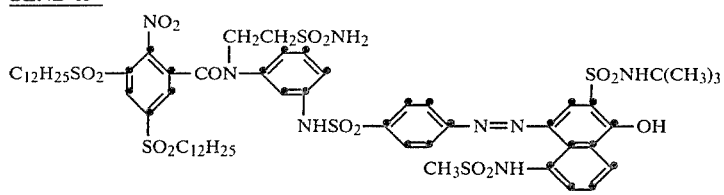
BEND-16
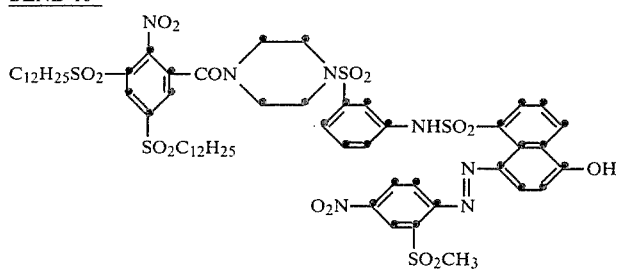
BEND-17
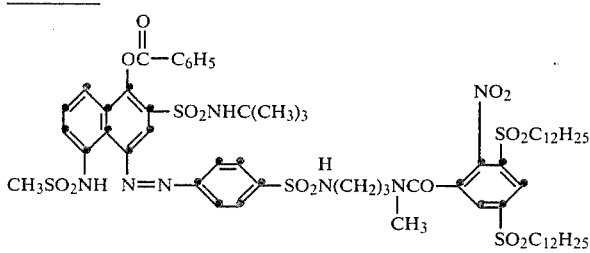
BEND-18
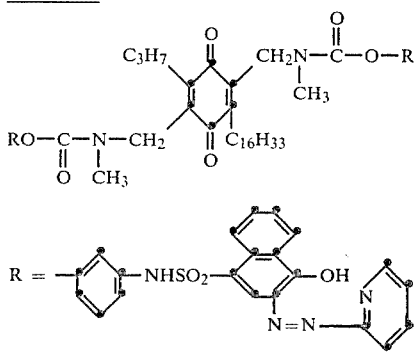
BEND-19
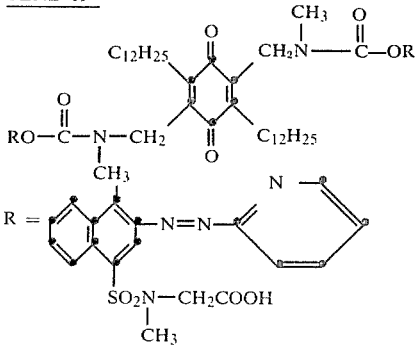
BEND-20

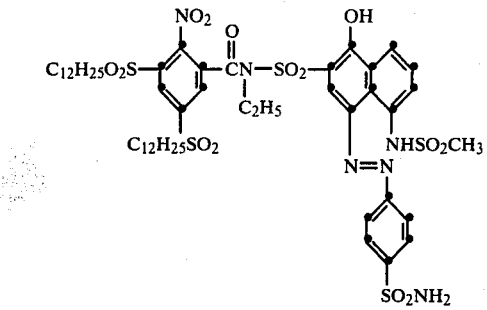
BEND-21
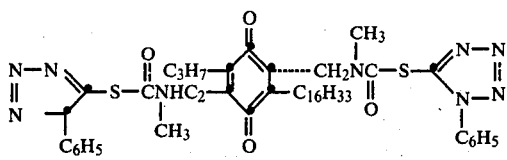
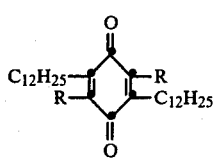
BEND 22
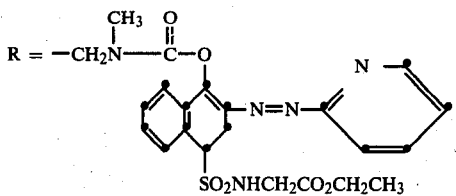
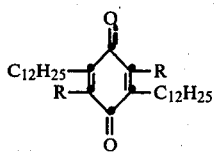
BEND-23
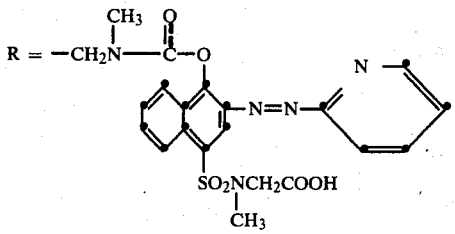
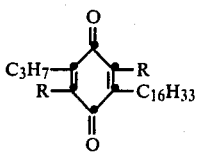
BEND-24
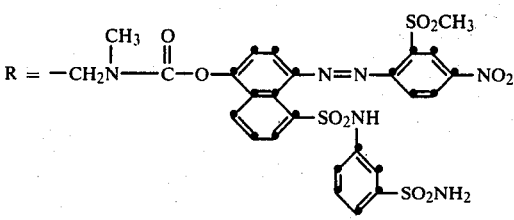
BEND-25

-continued
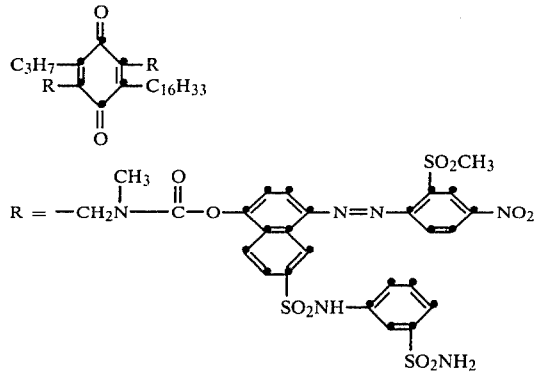
BEND-26
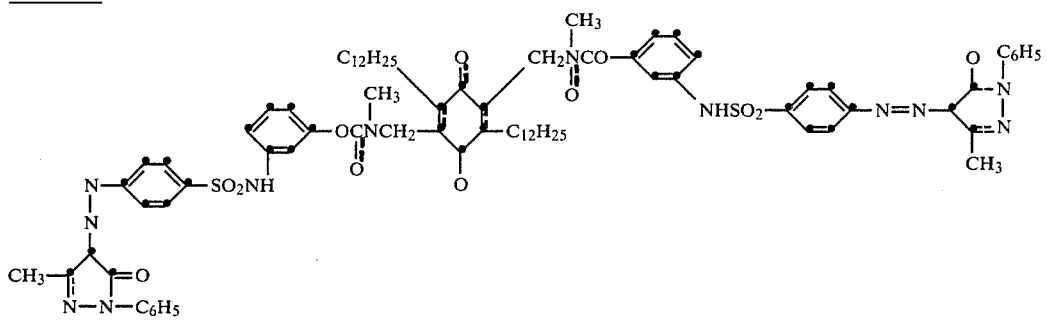
BEND-27
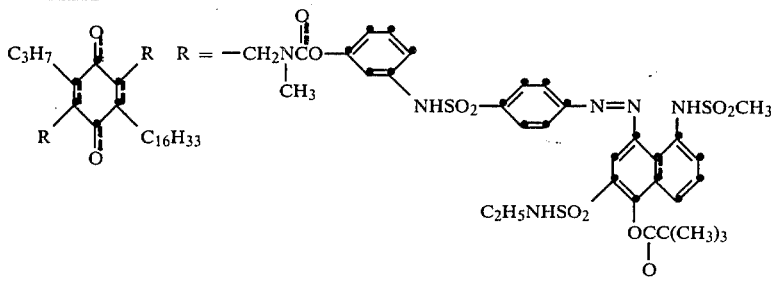
BEND-28
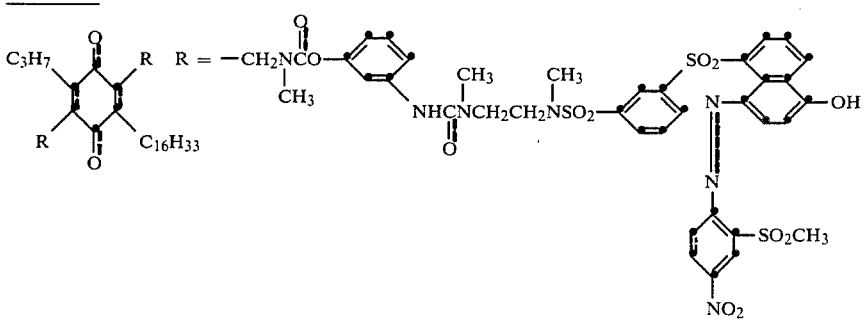
BEND-29
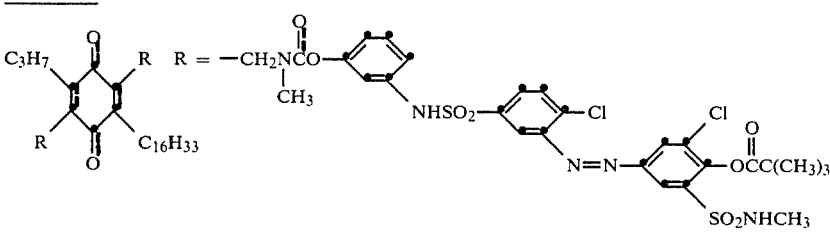
Typical useful photographic reagent-providing BEND compounds are as follows:

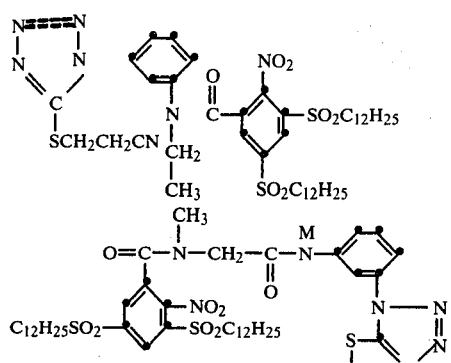

BEND-30

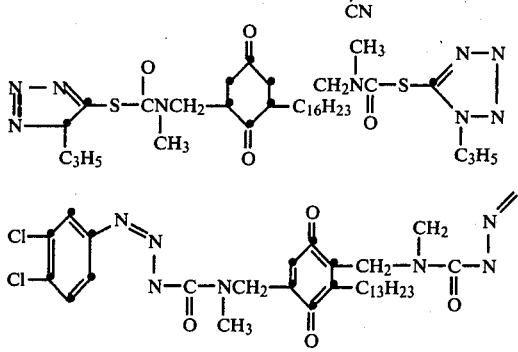

BEND-31

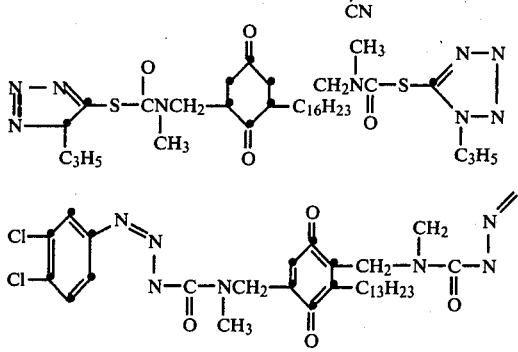

BEND-32

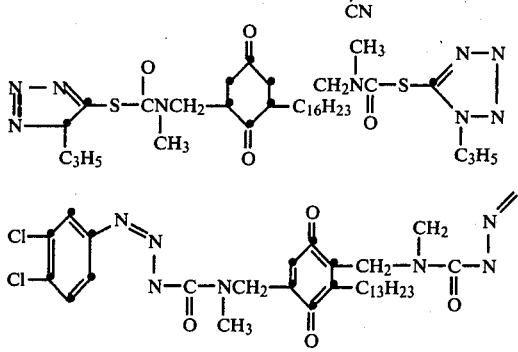

BEND-33

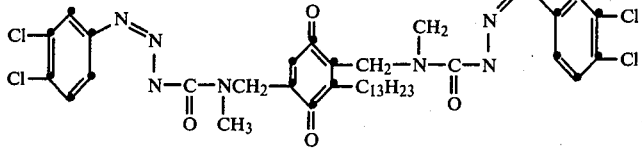

In photographic elements and film units with which the electron donor precursors of the invention are employed, the silver halide emulsion layers can be of any convenient conventional type, such as disclosed, for example, in Research Disclosure, Item 17643, Section 1, December 1978. Research Disclosure is published by Industrial Opportunities Ltd., Homewell Havant Hampshire, PO9 1EF United Kingdom. The emulsions can be either negative-working or positive-working emulsions and can form either a surface or internal latent image upon exposure.

As described in the above referenced Research Disclosure Item 17643, the emulsions can be chemically sensitized (Section III), be spectrally sensitized or desensitized (Section IV), be hardened (Section X), include stabilizers and antifoggants (Section VI), and contain other conventional photographic addenda.

In processing photographic elements and film units according to this invention as electron transfer agent (ETA) is employed. The ETA functions to develop the silver halide and provide a corresponding imagewise pattern of oxidized electron donor because the oxidized ETA readily accepts electrons from the electron donor. Generally, the useful ETA's will at least provide a faster rate of silver halide development under the conditions of processing when the combination of the electron donor and the ETA is employed as compared with the development rate when the electron donor is used in the process without the ETA.

Typical useful ETA compounds include hydroquinone compounds such as hydroquinone, 2,5-dichlorohydroquinone, 2-chlorohydroquinone and the like; aminophenol compounds such as 4-aminophenol, N-methylaminophenol, 3-methyl-4-aminophenol, 3,5-dibromoaminophenol and the like; catechol compounds such as catechol, 4-cyclohexylcatechol, 3-methoxycatechol, 4-(N-octadecylamino)catechol and the like; phenylenediamine compounds such as N,N-diethyl-p-phenylenediamine, 3-methyl-N,N-diethyl-p-phenylenediamine, 3-methoxy-N-ethyl-N-ethoxy-p-phenylenediamine, N,N,N',N'-tetramethyl-p-phenylenediamine and the like. In highly preferred embodiments, the ETA is a 3-pyrazolidone compound such as 1-phenyl-3-pyrazolidone, 1-phenyl-4,4-dimethyl-3-pyrazolidone, 4-hydroxymethyl-4-methyl-1-phenyl-3-pyrazolidone, 4-hydroxymethyl-4-methyl-1-(3,4dimethylphenyl)-3-pyrazolidone, 1-m-tolyl-3-pyrazolidone, 1-p-tolyl-3-pyrazolidone, 4-hydroxymethyl-4-methyl-1-p-tolyl-3-pyrazolidone, 1-phenyl-4-methyl-3-pyrazolidone, 1-phenyl-5-methyl-3-pyrazolidone, 1-phenyl-4,4bis-(hydroxymethyl)-3-pyrazolidone, 1,4-dimethyl-3-pyrazolidone, 4-methyl-3-pyrazolidone, 4,4-dimethyl-3-pyrazolidone, 1-(3-chlorophenyl)-4-methyl-3-pyrazolidone, 1-(4-chlorophenyl)-4-methyl-3-pyrazolidone, 1-(3-chlorophenyl)-3-pyrazolidone, 1-(4-chlor.phenyl)-3-pyrazolidone, 1-(4-tolyl)-4-methyl-3-pyrazolidone, 1-(2-tolyl)-4-methyl-3-pyrazolidone, 1-(4-tolyl)-3-pyrazolidone, 1-(3-tolyl)-3-pyrazolidone, 1-(3-tolyl)-4,4-dimethyl-3-pyrazolidone, 1-(2-trifluoroethyl)-4,4-dimethyl-3-pyrazolidone, 5-methyl-3-pyrazolidone and the like; etc. A combination of different ETA's such as those disclosed in U.S. Pat. No. 3,039,869 can also be employed. The particular ETA selected will, of course, depend on the particular electron donor and BEND used in the process and the processing conditions for the particular photographic element.

In practicing processes of this invention an alkaline environment is provided in which an element or film unit containing developable silver halide and a BEND compound is contacted with an electron donor and an electron transfer agent. Development of silver halide to silver generates oxidized electron donor as a result of a reaction between oxidized electron transfer agent and electron donor. The electron donor which has been oxidized is rendered incapable of reacting with the BEND compound to release diffusible dye or photographic reagent. Thus, the process results in a pattern of diffusible dye or photographic reagent which is inversely proportional to the amount of electron donor which has been oxidized.

In the case of dye-providing BEND compounds, the diffusible dye can be transferred to a receiving element and employed as a transfer image. Alternatively, it can merely be removed from the element. Whether the diffusible dye is employed to form a transfer image or not, the remaining BEND compound, from which dye has not been released, can be employed to form a retained image. Alternatively, it can be contacted with an additional amount of unoxidized electron donor to release diffusible dye which in turn can be employed to form a transfer image.

This processing sequence has been described with respect to a simple element which can comprise a support bearing a layer of the silver halide emulsion having associated therewith a dye providing BEND compound. Processing can be effected by contacting the element with an appropriate aqueous alkaline solution and effecting transfer by contacting the element during or subsequent to processing with a separate receiving element to effect transfer of the dye or by washing the element with an aqueous solution to remove dye. However, this process can be employed with film units which contain a receiver and some or all of the processing components. Such units are well known in the art of color diffusion.

In the case of photographic reagent-providing BEND compounds the photographic reagent is made available in an imagewise pattern and as an inverse function of silver halide development. This pattern can be used in any of the ways known to those skilled in the art for making use of such a pattern of reagent. For example, if the reagent is a development inhibitor, it can be used to suppress development of silver halide in background, non-image areas. If the photographic reagent-providing BEND compound is incorporated in a color photographic element or film unit, the dye image can be provided by any known dye-image providing material, such as a dye forming coupler, a dye providing BEND compound or a redox dye releaser, such as described in U.S. Pat. Nos. 4,055,428 and 4,076,529. BEND compounds which release development inhibitors are particularly useful with redox dye releasers, and contribute to improved image discrimination in elements containing such compounds, since they suppress development in areas where release of dye as a consequence of silver halide development is undesirable.

While photographic elements of this invention can be simple elements comprising a support bearing a silver halide emulsion layer having a BEND compound and electron donor precursor associated therewith, preferred are multilayer multicolor elements and film units.

A typical multilayer multicolor photographic element can comprise a support having thereon a red-sensitive silver halide emulsion unit having associated therewith a cyan-dye-image-providing material, a green-sensitive silver halide emulsion unit having associated therewith a magentadye-image-providing material and a blue-sensitive silver halide emulsion unit having associated therewith a yellow-dye-image-providing material, at least one of the silver halide emulsion units having a BEND compound associated therewith.

Each silver halide emulsion unit can be composed of one or more layers and the various units and layers can be arranged in different relationships with respect to one another in accordance with configurations known in the art.

The elements and film units can contain additional layers conventional in photographic elements, such as spacer layers, filter layers, antihalation layers, scavenger layers and the like. The support can be any suitable support used with photographic elements. Typical supports include polymeric films, paper (including polymercoated paper), glass and the like.

The BEND compounds can be incorporated in a silver halide layer, or in another layer of the photographic element or film unit where it will be in association with the silver halide emulsion layer. The BEND compound can be incorporated in these layers in the way photographic couplers are incorporated in such layers. Depending upon the physical properties of the BEND compound and its physical compatibility with th emulsion or vehicle, it can be dispersed directly therein, or it can be mixed with organic or aqueous solvents and then dispersed in the emulsion or vehicle. To obtain a visible image record with dye-providing BEND compounds they normally will be used in a concentration of about $1 \times 10^{-5}$ moles/m$^2$ to about $2 \times 10^{-3}$ moles/m$^2$. With photographic-reagent-providing BEND compounds the concentration employed will depend upon the particular reagent, the magnitude of the effect desired from it and the nature of other components in the film unit.

As indicated above, the electron donor precursor is preferably incorporated in the same layer as the BEND compound, particularly when it is of the semi-immobile type discussed above, although it can be incorporated in an adjacent layer or in the processing composition. When incorporated in the element or film unit, the electron donor is employed in a ratio of 1:2 to 2:1 and preferably 1:1 to 2:1 moles electron donor per mole BEND compound.

The electron transfer agent is preferably incorporated in the processing composition, although it can be in a layer of the element or film unit in a blocked or precursor form. When incorporated in the processing composition, the electron transfer agent is preferably present in a concentration of 0.5 to 40 gram/liter and most preferably 1.0 to 20 gram/liter.

When electron donor precursor and/or electron transfer agent is incorporated in the element or film unit, the processing composition serves to activate the component and/or provide a medium in which it can contact the silver halide or the BEND compound, or both.

The processing composition is an aqueous alkaline solution of a base, such as an alkali metal hydroxide or carbonate (e.g., sodium hydroxide or sodium carbonate) or an amine (e.g. diethylamine). Preferably the alkaline composition has a pH in excess of 11. Suitable materials for use in such compositions are disclosed in *Research Disclosure*, pages 79–80, November 1976.

Preferably, the alkaline processing composition is introduced into reactive association with other components of the film unit from a rupturable container which is adapted to be positioned during processing of the film unit so that a compressive force applied to the container by pressure-applying members will rupture the container and effect a discharge of the containers contents within the film unit. However, other methods of introducing the alkaline processing composition can be employed.

Preferred rupturable containers are described in U.S. Pat. Nos. 2,543,181; 2,643,886; 2,653,732; 2,723,051; 3,056,492; 3,056,491 and 3,152,515. In general, such containers comprise a rectangular sheet of fluid- and air-impervious material folded longitudinally upon itself to form two walls which are sealed to one another along their longitudinal and end margins to form a cavity in which processing solution is contained.

Any material can be employed as the image-receiving layer in the film units of this invention as long as it will mordant, or otherwise fix, the dyes which diffuse to it. The particular material chosen will, of course, depend upon the dyes to be mordanted. The image-receiving layer can contain ultraviolet absorbers to protect the dye images from fading due to ultraviolet light, brighteners and similar materials used to protect or enhance photographic dye images.

Additional layers can be incorporated in film units of this invention. These include pH lowering layers (sometimes referred to as acid layers or neutralizing layers), timing or spacing layers, opaque light-reflecting layers, opaque light-absorbing layers, scavenger layers, and the like.

Various formates for diffusion transfer film units are known in the art. The layer arrangement employed with them can be used in the film units of this invention. In one useful format the dye image-receiving layer of the film unit is located on a separate support adapted to be superposed on the photographic element after exposure thereof. Such image-receiving layers are generally disclosed, for example, in U.S. Pat. No. 3,362,819.

In another useful format the dye image-receiving layer is located integral with the photographic element and is positioned between the support and the lowermost silver halide emulsion layer. One such format is disclosed in Belgian Pat. No. 757,960. In such a format, the support for the photographic element is transparent and bears in order, an image-receiving layer, a substantially opaque light-reflective layer, and then the photosensitive layer or layers. After imagewise exposure, a rupturable container containing the alkaline processing composition and an opaque process sheet are brought into superposed position. Pressure-applying members in the camera rupture the container and spread processing composition over the photographic element as the film unit is withdrawn from the camera. The processing composition develops each exposed silver halide emulsion layer and dye images, formed as a function of development, diffuse to the image-receiving layer to provide a right-reading image which is viewed through the transparent support on the opaque reflecting layer backgrounds. For other details concerning the format of this particular integral film unit, reference is made to the above-mentioned Belgian Pat. No. 757,960.

Another format is disclosed in Belgian Pat. No. 757,959. In this embodiment, the support for the photographic element is transparent and bears, in order, the image-receiving layer, a substantially opaque, light-reflective layer and the photosensitive layer or layers. A rupturable container, containing an alkaline processing composition and an opacifier, is positioned between the uppermost emulsion layer and a transparent top sheet which has thereon a neutralizing layer and a timing layer. The film unit is placed in a camera exposed through the transparent top sheet and then passed through a pair of pressure-applying members in the camera as it is being removed therefrom. The pressure-applying members rupture the container and spread processing composition and opacifier over the photographic layers to commence development and protect the photosensitive layers from further light exposure. The processing composition develops each silver halide layer and dye images, formed as a result of development, diffuse to the image-receiving layer to provide a right-reading image which is viewed through the transparent support on the opaque reflecting layer background. For further details concerning the format of this particular integral film unit, reference is made to the above-mentioned Belgian Pat. No. 757,959.

Still other useful formats in which this invention can be employed are described in U.S. Pat. Nos. 3,415,644; 3,415,645; 3,415,646; 3,647,437; 3,635,707; and 3,993,486.

The term "nondiffusible" used herein has the meaning commonly applied to the term in photography and denotes materials that for all practical purposes do not migrate nor wander through organic colloid layers such as gelatin in an alkaline medium, in the photographic elements of the invention and preferably when processed in a medium having a pH of 11 or greater. The same meaning is to be attached to the term "immobile." The term "diffusible" as applied to the materials of this invention has the converse meaning and denotes materials having the property of diffusing effectively through the colloid layers of the photographic elements in an alkaline medium. "Mobile" has the same meaning.

The term "associated therewith" as used herein is intended to mean that the materials can be in either the same or different layers so long as the materials are accessible to one another during processing.

The following examples further illustrate this invention.

EXAMPLE 1—N-($\alpha$-(Ethoxycarbonyl)phenacyl]saccharin (Compound 3)

To a solution of 41.5 g (0.2 M) of sodium saccharin in 250 ml of dimethylformamide was added 1 equivalent of ethyl bromobenzoylacetate (prepared quantitatively from bromination of ethyl benzoylacetate in methylene chloride at room temperature). The mixture was stirred at ambient temperature for several days and poured into 1.5 liter of water. The precipitated solid was washed with water and recrystallized from ethanol to give 62 g (83%) of Compound 3: mp 139.6° C.

EXAMPLE 2—N-(p-methoxy)phenacylsaccharin (Compound 6)

To a solution of 0.05 M of sodium saccharin in 50 ml of dimethylformamide was added 1 equivalent of p-methoxyphenacyl bromide. The solution was treated as in Example 1 followed by recrystallization from benzene and hexane (2:1 v/v), to give 16 g (97%) of Compound 6: mp 165.7° C.

EXAMPLE 3—N-[$\alpha$-(Methyl)phenacyl]saccharin (Compound 5)

To a solution of 0.05 M of sodium saccharin in 50 ml of dimethylformamide was added 1 equivalent of $\beta$-bromopropiophenone. The solution was stirred at room temperature overnight and was treated as in Example 1.

Recrystallization from benzene and hexane afforded 13 g (83%) of Compound 5: mp 158.6° C.

EXAMPLE 4—N-(p-phenyl)phenacylsaccharin (Compound 7)

To a solution of 10.2 g (0.05 M) of sodium saccharin in 150 ml of dimethylformamide at room temperature was added 1 equivalent of p-(phenyl)phenacyl bromide. After stirring at ambient temperature overnight, the reaction mixture was treated as in Example 1 to give 16 g (85%) of Compound 7: mp 190.0° C.

EXAMPLE 5—N—[m-hexadecanesulfonamido)phenacyl]saccharin (Compound 24)

A. m-(Hexadecanesulfonamido)acetophenone)

To a mechanically stirred solution of 31.2 g (0.23 M) of m-aminoacetophenone and 35.4 ml (0.254 M) of triethylamine in 1 liter of tetrahydrofuran was added 75 g (0.23 M) of 1-hexadecanesulfonyl chloride at room temperature. The mixture was stirred for 2 hours and the suspended salt was removed. The filtrate was treated on a rotary evaporator to give a solid which was recrystallized from hexane: mp 95.5°–100° C.

B. m-(Hexadecanesulfonamido)bromoacetophenone

Bromine, 4.72 g (1.52 ml) was added to 25 g (0.059 M) of the product of Step A in 75 ml of glacial acetic acid at 70° C. Decolorization of bromine was instant. The reaction was followed by thin layer chromatography ($CH_2Cl_2$, silica gel) until the starting material was practically absent. The solid precipitated on cooling was collected by filtration, recrystallized from hexane to give 23.5 g of product (about 80% based on m-aminoacetophenone): mp 92°–5° C. Mass spectrum showed some dibrominated material.

C. Compound 24

A mixture of 4.5 g of sodium saccharin and 10 g of the product of Step B in 70 ml of dimethylformamide was stirred overnight at ambient temperature. The reaction mixture was poured in brine and icy water (about 600 ml) and the precipirated product was filtered, and recrystallized from 200 ml of methanol to give 12 g (100%) of Compound 24: mp 85.9° .

EXAMPLE 6—6-Amino-N-(p-methoxyphenacyl)saccharin (Compound 22)

The sodium salt of 6-aminosaccharin was prepared by reacting the latter (1 g) with 1 equivalent (270 mg) of sodium methylate in 15 ml of methanol. The methanol was removed under vacuum, and the residue was dissolved in 15 ml of dimethylformamide, to which 1.16 g of p-methoxyphenacyl bromide was added at room temperature. The solution was stirred overnight, poured into 500 ml of brine and water. The precipirated solid was filtered, washed with water, air-dried, and recrystallized from 20 ml of 1,1,2-trichloroethane to give 760 mg of Compound 22: mp 248.3° C.

EXAMPLE 7—N-(p-Carboxyphenacyl)saccharin

To a solution of 15 g (0.061 M) of p-(carboxy)-bromoacetophenone in dimethylformamide was added 45 g (excess) of sodium saccharin. The mixture was stirred at room temperature until a thin layer chromatography showed the disappearance of starting material. The solution was then treated with dilute hydrochloric acid (1500 ml). The precipitated solid was filtered, washed with water, and recrystallized from acetic acid to give 34 g of the title product. The acid chloride of this product was prepared by oxalyl chloride/dimethylformamide reaction in tetrahydrofuran. This acid chloride was used without further purification to prepare Compounds 27, 30 and 31 using the appropriate amines in the presence of triethylamine in methylene chloride.

EXAMPLE 8

Polarographic halfwave potentials of representative electron donor precursors were measured in 0.1 N sodium hydroxide versus a saturated calomel electrode. Results are reported in Table I below.

TABLE I

| Compound | $-E_{\frac{1}{2}}$(volt) |
| --- | --- |
| 1 | 0.54 |
| 3 | 0.31 |
| 6 | 0.58 |
| 8 | 0.34 |
| 9 | 0.32 |
| 10 | 0.31 |
| 12 | 0.55 |
| 13 | 0.48 |
| 14 | 0.48 |
| 15 | 0.50 |
| 17 | 0.56 |
| 18 | 0.56 |
| 19 | 0.55 |
| 23 | 0.58 |
| 24 | 0.59 |
| 28 | 0.54 |
| 30 | 0.55 |

EXAMPLE 9

A series of photographic elements was prepared having incorporated therein a magenta-dye-providing BEND compound and various electron donor precursors.

Each element was prepared by coating a poly(ethylene terephthalate) film support with a layer containing gelatin at 200 mg/ft$^2$ (2.7 g/m$^2$); a negative-working silver bromide emulsion at 100 mg Ag/ft$^2$ (1.08 g Ag/m$^2$); BEND Compound 27 at $1.75 \times 10^{-5}$ moles/ft$^2$ ($1.89 \times 10^{-4}$ moles/m$^2$) and an electron donor precursor of the invention (see Table II) at $7.0 \times 10^{-5}$ moles/ft$^2$ ($7.56 \times 10^{-4}$ moles/m$^2$). The BEND compound and the electron donor precursor were dissolved in an equal weight of diethyllauramide and dispersed together in gelatin before coating. A suitably hardened overcoat layer containing gelatin at 50 mg/ft$^2$ (0.54 g/m$^2$) and bis(vinylsulfonylmethyl) ether at 3.0 mg/ft$^2$ (3.24 mg/m$^2$) was then applied.

To determine the dye release rate ($t_{\frac{1}{2}}$ in minutes), the silver halide was removed from samples of each element by treatment, for 1 minute in a fixing solution comprising 120 g of ammonium thiosulfate, 20 g of potassium metabisulfite and water to make 1.0 liter, followed by a water wash and drying.

The samples were then laminated to samples of a receiver element, which contained a mordant for the diffusible dye moiety released from the BEND compound; and a portion of a viscous activator solution comprising 51 g of potassium hydroxide, 3.0 g of 4-hydroxymethyl-4-methyl-1-phenyl-3-pyrazolidone and 40 g of carboxymethyl cellulose per liter of water was spread between the elements.

Separate samples were separated at 1, 3, 5, 10 and 20 minutes, respectively, and their corresponding receiver elements were then washed in water and dried. A plot of the transferred dye densities vs. time of lamination was made to determine the rate of dye release ($t_{1/2}$) recorded in Table II.

Since all of the electron donor precursors of the invention were not tested simultaneously, each run included a control, wherein the electron donor precursor was a ballasted benzisoxazolone Compound A, shown below. For direct comparison, the release-rate determined with each control sample is listed in Table II.

Compound A

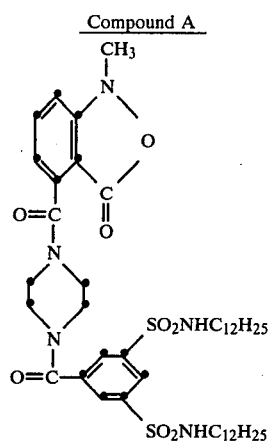

TABLE II

| Coating Number | Electron Donor Precursor | Dye Release Rate (seconds) $t_{1/2}$ | $t_{1/2}$(control) |
|---|---|---|---|
| 1 | 7 | 150 | 300 |
| 2 | 17 | 60 | 300 |
| 3 | 21 | > 7 min | 320 |
| 4 | 23 | >10 min | 300 |
| 5 | 24 | 90 | 250 |
| 6 | 26 | 50 | 300 |
| 7 | 30 | 90 | 350 |
| 8 | 31 | 75 | 300 |
| 9 | 32 | 280 | 280 |

This invention has been described in detail with particular reference to preferred embodiments thereof, but it will be understood that variations and modifications can be effected within the spirit and scope of the invention.

What is claimed is:

1. In a photographic element processable by means of an alkaline processing composition, the element comprising a support, a silver halide emulsion having associated therewith an immobile compound which upon reduction under alkaline conditions will release a diffusible dye or photographic reagent, and an electron donor precursor, the improvement wherein the electron donor precursor comprises a compound represented by the structural formula:

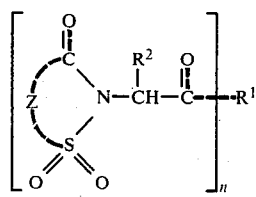

wherein:

Z represents the atoms to complete a bi- or tricyclic ring system, each ring of which contains 5 to 6 nuclear atoms;

n is 1 or 2;

$R^1$ is a monovalent aromatic group when n is 1 and a bivalent aromatic group when n is 2; and $R^2$ represents hydrogen, an alkyl group, an aryl group, an acyl group, an ester group or an amido group.

2. A photographic element of claim 1 wherein the electron donor precursor comprises a compound represented by the structural formula:

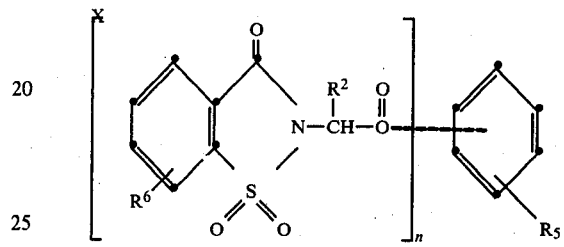

wherein:

n is 1 or 2;

$R^6$ is hydrogen, halogen, amino, nitro, cyano, alkyl of 1 to 30 carbon atoms, alkoxy of 1 to 30 carbon atoms, aryl of 6 to 30 carbon atoms, aryloxy of 6 to 30 carbon atoms, acyl, ester or amido;

$R^5$ is hydrogen, halogen, nitro, amino, cyano, alkyl of 1 to 30 carbon atoms, alkoxy of 1 to 30 carbon atoms, aryl of 6 to 30 carbon atoms, aryloxy of 6 to 30 carbon atoms, acyl, ester or amido, provided that sulfonamido, carbonamido or phosphoramido substituents are not in the 4-position of the aromatic group; and $R^2$ is hydrogen, alkyl of 1 to 30 carbon atoms, aryl of 6 to 30 carbon atoms, acyl, ester or amido.

3. A photographic element of claim 4 wherein
n is 1;

$R^2$ is hydrogen or alkyl of 1 to 4 carbon atoms;

$R^5$ is hydrogen, halogen, nitro, alkyl of 1 to 30 carbon atoms, phenyl, acyl, ester or amido, provided that if $R^5$ is sulfonamido, carbonamido or phosphoramido it is in the ortho or meta position; and $R^6$ is hydrogen, acyl, ester or amido.

4. A photographic element of claim 2 or 3 wherein $R^2$, $R^5$ and $R^6$ are so chosen that the electron donor precursor is dispersible in aqueous coating compositions and is at least semi-immobile in the alkali-permeable layers of the element.

5. In a photographic element processable by means of an alkaline processing composition, the element comprising a support, a silver halide emulsion having associated therewith an immobile compound which upon reduction under alkaline conditions will release a diffusible dye or photographic reagent, and an electron donor precursor, the improvement wherein the electron donor precursor comprises a compound represented by the structural formula:

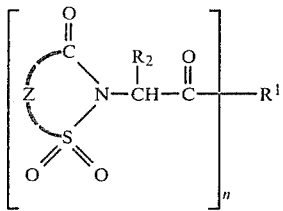

wherein
n is 1 or 2;
Z is phenylene or naphthylene which is unsubstituted or substituted with one or more halogen, amino, nitro, cyano, alkyl of 1 to 30 carbon atoms, alkoxy of 1 to 30 carbon atoms, aryl of 6 to 30 carbon atoms, aryloxy of 6 to 30 carbon atoms, acyl, ester or amido group;
$R^1$ is phenyl, phenylene, biphenylyl, biphenylylene, naphthyl, naphthylene, anthryl or anthrylene which is unsubstituted or substituted with one or more halogen, nitro, amino, cyano, alkyl of 1 to 30 carbon atoms, alkoxy of 1 to 30 carbon atoms, aryl of 6 to 30 carbon atoms, aryloxy of 6 to 30 carbon atoms, acyl, ester or amido groups, provided that sulfonamido, carbonamido or phosphoramido substituents are not in the 4-position of the aromatic group; and
$R^2$ is hydrogen, alkyl of 1 to 30 carbon atoms, aryl of 6 to 30 carbon atoms, acyl, ester or amido.

6. A photographic element of claim 5 wherein R, Y and Z are so chosen that the electron donor precursor is dispersible in aqueous coating compositions and is at least semi-immobile in alkali-permeable layers of the element.

7. An element of claim 5 wherein the immobile compound is a BEND compound represented by the structural formula:

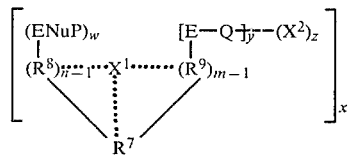

wherein:
w, x, y, z, n and m are positive integers of 1 or 2;
ENuP is an electron-accepting nucelophilic precursor group;
$R^7$ is a cyclic organic group to which ENuP and E are attached;
$R^8$ and $R^9$ are bivalent organic groups containing from 1 to 3 atoms in the bivalent linkage;
E and Q provide an electrophilic cleavage group where
E is an electrophilic group and
Q is a bivalent amino group, oxygen atom, selenium atom or sulfur atom providing a monoatom linkage between E and $X^2$ and which is displaceable from E by the nucleophilic group provided by ENuP;
$X^1$ is a substituent on at least one of $R_7$, $R^8$ and $R^9$; and
one of $X^1$ or $Q—X^2$ is a ballasting group of sufficient size to render said compound immobile in an alkali-permeable layer of a photographic element, and one of $X^1$ and $Q—X^2$ is a diffusible image dye-providing material or a diffusible photographic reagent.

8. An element of claim 7 wherein $Q—X^2$ provides, upon release, a diffusible image dye.

9. An element of claim 7 wherein $Q—X^2$ provides, upon release, a diffusible photographic reagent.

10. An element of claim 7 wherein the BEND compound is represented by the structural formula:

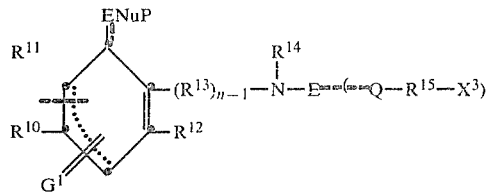

wherein:
ENuP is an electron-accepting nucleophilic precursor for a hydroxy nucleophilic group;
$G^1$ is an amino group, a cyclic group formed with $R^{10}$ or $R^{12}$ or any of the groups specified for ENuP;
E is an electrophilic group;
Q is a bivalent amino group, an oxygen atom, a sulfur atom or a selenium atom providing a mono atom linkage between E and $R^{15}$;
$R^{13}$ is a bivalent group containing from 1–3 carbon atoms in the bivalent linkage;
n is an integer of 1 or 2;
$R^{15}$ is an aromatic group containing from 5–20 atoms or an alkylene group containing from 1–12 carbon atoms;
$R^{14}$ is an alkyl group containing from 1-40 carbon atoms, an aryl group containing from 6-40 carbon atoms, or the substituent $X^1$;
$R^{12}$, $R^{10}$, and $R^{11}$ are each hydrogen, halogen, an alkyl group, an alkoxy group, an aryl group containing from 6-40 carbon atoms, a carbonyl group, a sulfamyl group, a sulfonamido group, the substituent $X^1$, or $R^{12}$ and $R^{11}$ or $R^{10}$ and $R^{11}$, when they are on adjacent positions of the ring, may be taken together to form a 5- to 7-membered ring with the remainder of the molecule with the provision that, when $R^{15}$ is an alkylene group, $R^{12}$ and $R^{10}$ are poly atom groups, and when $G^1$ is an electron-accepting nucleophilic precursor group as defined for ENuP, the $R^{10}$ or $R^{12}$ substituent adjacent $G^1$ can be the group:

$X^1$ is provided in at least one of the substituted positions and each of $X^1$ and $--(--Q—R^{15}—X^3)$ is ballasting group of sufficient size to render said compound immobile in an alkali-permeable layer of a photographic element, or an image dye providing material or a photographic reagent, provided one of $X^1$ and $--(--Q—R^{15}—X^3)$ is ballast group and the other is an image dye providing material or a photo-graphic reagent.

11. An element of claim 7 wherein the BEND compound is represented by the structural formula:

$$\left[ [(R^{16})_{\overline{q-1}} W]_{\overline{p-1}} \underbrace{\overset{ENuP}{\underset{(X^1)_{p-1}}{A}}}_{} (R^{17})_{\overline{m-1}} [\!-\!Q\!-\!-\!-\!X^2 \right]_n$$

where:

ENuP is an electron-accepting precursor for a hydroxylamino group;

A is a group containing the atoms necessary to form a 5- or 6-membered aromatic ring;

W is an electron-withdrawing group having a positive Hammett sigma value;

$R^{16}$ is a hydrogen atom, an alkyl group containing from 1-30 carbon atoms, or an aryl group containing from 6-30 carbon atoms;

$R^{17}$ is a bivalent organic group containing from 1-3 atoms in the bivalent linkage;

m and q are positive integers of 1 or 2;

p and r are positive integers, with $[(R^{16})_{\overline{q-1}} W]$ being a substituent on any portion of the aromatic-ring structure of A;

E and Q provide an electrophilic cleavage group where E is an electrophilic center and Q is a group providing a monoatom linkage between E and $X^2$;

n is an integer of 1-3;

$X^2$, together with Q, is either an image dye-providing material, an image-dye precursor or a photographic reagent; and $X^1$ is a ballasting group of sufficient size to render said BEND compound immobile and nondiffusible in the alkali-permeable layers of a photographic element.

12. In an image transfer film unit processable with an alkaline processing composition containing an electron transfer agent, the film unit comprising:

(a) a photographic element comprising a support and a silver halide emulsion having associated therewith an immobile compound which upon reduction under alkaline conditions will release a diffusible dye or photographic reagent;

(b) an image-receiving layer; and (c) an electron donor precursor; the improvement wherein the electron donor precursor comprises a compound represented by the structural formula:

$$\left[ \begin{array}{c} \overset{O}{\underset{}{\overset{\|}{C}}} \\ Z \diagup \diagdown N\!-\!CH\!-\!\overset{O}{\underset{}{\overset{\|}{C}}}\!-\!R^1 \\ \diagdown \diagup \\ S \\ \overset{\diagup\!\diagdown}{O \quad O} \end{array} \right]_n$$

wherein:

Z represents the atoms to complete a bi- or tricyclic ring system, each ring of which contains 5 to 6 nuclear atoms;

n is 1 or 2;

$R^1$ is a monovalent aromatic group when n is 1 and a bivalent aromatic group when n is 2; and $R^2$ represents hydrogen, an alkyl group, an aryl group, an acyl group, an ester group or an amido group.

13. In an image transfer film unit comprising:

(a) a photographic element comprising a support and a silver halide emulsion layer having associated therewith an immobile compound which upon reduction under alkaline conditions will release a diffusible dye or photographic reagent;

(b) an image-receiving layer;

(c) an alkaline processing composition contained within means from which it can be discharged within the film unit;

(d) an electron transfer agent and (e) an electron donor precursor; the improvement wherein the electron donor precursor comprises a compound represented by the structural formula:

$$\left[ \begin{array}{c} \overset{O}{\underset{}{\overset{\|}{C}}} \\ Z \diagup \diagdown N\!-\!CH\!-\!\overset{O}{\underset{}{\overset{\|}{C}}}\!-\!R^1 \\ \diagdown \diagup \\ S \\ \overset{\diagup\!\diagdown}{O \quad O} \end{array} \right]_n$$

wherein:

Z represents the atoms to complete a bi- or tricyclic ring system, each ring of which contains 5 to 6 nuclear atoms;

n is 1 or 2;

$R^1$ is a monovalent aromatic group when n is 1 and a bivalent aromatic group when n is 2; and $R^2$ represents hydrogen, an alkyl group, an aryl group, an acyl group, an ester group or an amido group.

14. A film unit of claim 13 wherein the electron donor precursor is in the same layer as the immobile compound.

15. A film unit of claim 14 wherein the electron donor precursor is substantially immobile in the alkali permeable layers of the film unit.

16. A film unit of claim 15 wherein Z is vinylene phenylene or naphthylene which is unsubstituted or substituted with one or more halogen, amino, nitro, cyano, alkyl of 1 to 30 carbon atoms, alkoxy of 1 to 30 carbon atoms, aryl of 6 to 30 carbon atoms, aryloxy of 6 to 30 carbon atoms, acyl, ester or amido groups;

$R^1$ is phenyl, phenylene, biphenylyl, biphenylylene, naphthyl, naphthylene, anthryl or anthrylene which is unsubstituted or substituted with halogen, nitro, amino, cyano, alkyl of 1 to 30 carbon atoms, alkoxy of 1 to 30 carbon atoms, aryl of 6 to 30 carbon atoms, aryloxy of 6 to 30 carbon atoms, acyl, ester or amido groups provided that sulfonamido, carbonamido or phosphoramido substituents are not in the 4-position of the aromatic group; and $R^2$ is hydrogen, alkyl of 1 to 30 carbon atoms, aryl of 6 to 30 carbon atoms, acyl, ester or amido.

17. A film unit of claim 15 wherein the electron donor precursor comprises a compound represented by the structural formula:

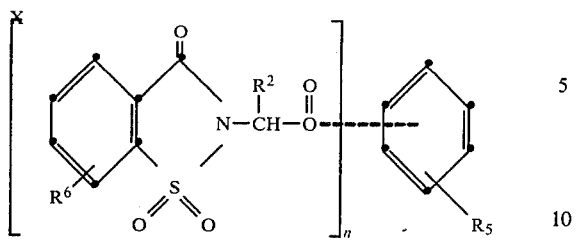

wherein:

n is 1 or 2;

R⁶ is hydrogen, halogen, amino, nitro, cyano, alkyl of 1 to 30 carbon atoms, alkoxy of 1 to 30 carbon atoms, aryl of 6 to 30 carbon atoms, aryloxy of 6 to 30 carbon atoms, acyl, ester or amido;

R⁵ is hydrogen, halogen, nitro, amino, cyano, alkyl of 1 to 30 carbon atoms, alkoxy of 1 to 30 carbon atoms, aryl of 6 to 30 carbon atoms, aryloxy of 6 to 30 carbon atoms, acyl, ester or amido, provided that sulfonamido, carbonamido or phosphoramido substituents are not in the 4-position of the aromatic group; and R² is hydrogen, alkyl of 1 to 30 carbon atoms, aryl of 6 to 30 carbon atoms, acyl, ester or amido.

18. A film unit of claim 17 wherein
n is 1;
R² is hydrogen or alkyl of 1 to 4 carbon atoms;
R⁵ is hydrogen, halogen, nitro, alkyl of 1 to 30 carbon atoms, phenyl, acyl, ester or amido, provided that if R⁵ is sulfonamido, carbonamido or phosphoramido it is in the ortho or meta position; and
R⁶ is hydrogen, acyl, ester or amido.

19. A film unit of claim 15 wherein the immobile compound is a BEND compound represented by the structural formula:

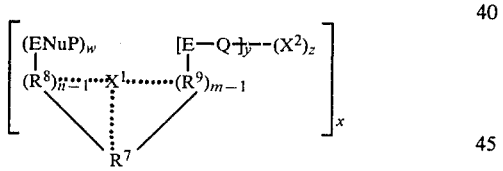

wherein:
w, x, y, z, n and m are positive integers of 1 or 2;
ENuP is an electron-accepting nucleophilic precursor group;
R⁷ is a cyclic organic group to which ENuP and E are attached;
R⁸ and R⁹ are bivalent organic groups containing from 1 to 3 atoms in the bivalent linkage;
E and Q provide an electrophilic cleavage group where
  E is an electrophilic group and
  Q is a bivalent amino group, oxygen atom, selenium atom or sulfur atom providing a monoatom linkage between E and X² and which is displaceable from E by the nucleophilic group provided by ENuP;
X¹ is a substituent on at least one of R⁷, R⁸ and R⁹; and
one of X¹ or Q-X² is a ballasting group of sufficient size to render said compound immobile in an alkali-permeable layer of a photographic element, and one of X¹ and Q-X² is a diffusible image dye-providing material or a diffusible photographic reagent.

20. In an image transfer film unit comprising:
(a) a photographic element comprising a support and at least one silver halide emulsion layer having associated therewith a BEND compound having the structural formula:

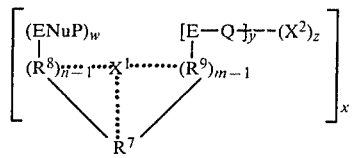

wherein:
w, x, y, z, n and m are positive integers of 1 or 2;
ENuP is an electron-accepting nucleophilic precursor group;
R⁷ is a cyclic organic group to which ENuP and E are attached;
R⁸ and R⁹ are bivalent organic groups containing from 1 to 3 atoms in the bivalent linkage;
E and Q provide an electrophilic cleavage group where
  E is an electrophilic group and
  Q is a bivalent amino group, oxygen atom, selenium atom or sulfur atom providing a monoatom linkage between E and X² and which is displaceable from E by the nucleophilic group provided by ENuP;
X¹ is a substituent on at least one of R⁷, R⁸ and R⁹; and
one of X¹ or Q-X² is a ballasting group of sufficient size to render said compound immobile in an alkali-permeable layer of a photographic element, and one of X¹ and Q-X² is a diffusible image dye-providing material;
(b) an image-receiving material;
(c) an alkaline processing composition contained within means from which it can be discharged within the film unit;
(d) an electron transfer agent and
(e) an electron donor precursor; the improvement wherein there is associated with the BEND compound an electron donor precursor represented by the structural formula:

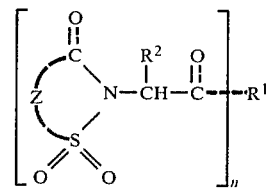

wherein:
Z represents the atoms of complete a bi- or tricyclic ring system, each ring of which contains 5 to 6 nuclear atoms;
n is 1 or 2;
R¹ is a monovalent aromatic group when n is 1 and a bivalent aromatic group when n is 2; and
R² represents hydrogen, an alkyl group, an aryl group, an acyl group, an ester group or an amido group.

21. A film unit of claim 20 wherein the photographic element comprises a blue-sensitive silver halide emulsion layer having associated therewith a BEND compound wherein Q—$X^2$ is a diffusible yellow dye moiety, a green-sensitive silver halide emulsion layer having associated therewith a BEND compound wherein Q—$X^2$ is a diffusible magenta dye moiety, and a red sensitive silver halide emulsion layer having associated therewith a BEND compound wherein Q—$X^2$ is a diffusible cyan dye moiety.

22. A film unit of claim 21 wherein each of said diffusible dye moieties is a diffusible azo dye moiety.

23. A film unit of claim 22 wherein each of said BEND compounds has the structure:

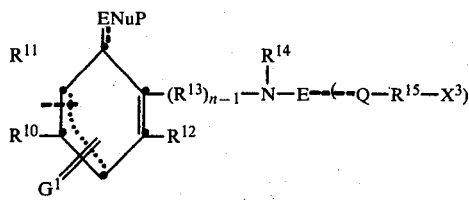

wherein:
ENuP is an electron-accepting nucleophilic precursor for a hydroxy nucleophilic group;
$G^1$ is an imino group, a cyclic group formed with $R^{10}$ or $R^{12}$ or any of the groups specified for ENuP;
E is an electrophilic group;
Q is a bivalent amino group, an oxygen atom, a sulfur atom or a selenium atom providing a mono atom linkage between E and $R^{15}$;
$R^{13}$ is a bivalent group containing from 1—3 carbon atoms in the bivalent linkage;
n is an integer of 1 or 2;
$R^{15}$ is an aromatic group containing from 5-20 atoms or an alkylene group containing from 1-12 carbon atoms;
$R^{14}$ is an alkyl group containing from 1-40 carbon atoms, an aryl group containing from 6-40 carbon atoms, or the substituent $X^1$;
$R^{12}$, $R^{10}$, and $R^{11}$ are each hydrogen, halogen, an alkyl group, an alkoxy group, an aryl group containing from 6 to 40 carbon atoms, a carbonyl group, a sulfamyl group, a sulfonamido group, the substituent $X^1$, or $R^{12}$ and $R^{11}$ or $R^{10}$ and $R^{11}$, when they are on adjacent positions of the ring, may be taken together to form a 5- to 7-membered ring with the remainder of the molecule with the provision that, when $R^{15}$ is an alkylene group, $R^{12}$ and $R^{10}$ are poly atom groups, and when $G^1$ is an electron-accepting nucleophilic precursor group as defined for ENuP, the $R^{10}$ or $R^{12}$ substituent adjacent $G^1$ can be the group:

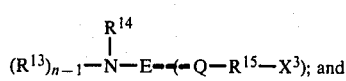

$X^1$ is provided in at least one of the substituted positions and is a ballasting group of sufficient size to render said compound immobile in an alkali-permeable layer of a photographic element, and --(--Q—$R^{15}$-$X^3$) is said diffusible azo dye moiety.

24. A film unit of claim 23 wherein ENuP and $G^1$ are each oxo groups.

25. A film unit of claim 24 wherein E is a carbonyl group and Q is an oxygen atom.

26. A film unit of claim 22 wherein each of said BEND compounds has the structure:

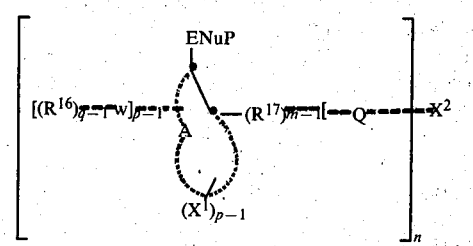

where:
ENuP is an electron-accepting precursor for a hydroxylamino group;
A is a group containing the atoms necessary to form a 5- or 6-membered aromatic ring;
W is an electron-withdrawing group having a positive Hammett sigma value;
$R^{16}$ is a hydrogen atom, an alkyl group containing from 1-30 carbon atoms, or an aryl group containing from 6-30 carbon atoms;
$R^{17}$ is a bivalent organic group containing from 1-3 atoms in the bivalent linkage;
m and q are positive integers of 1 or 2;
p and r are positive integers, with [($R^{16}$)$_{q-1}$W] being a substituent on any portion of the aromatic-ring structure of A;
E and Q provide an electrophilic cleavage group where E is an electrophilic center and Q is a group providing a monoatom linkage between E and $X^2$;
n is an integer of 1-3;
$X^2$, together with Q, is said diffusible azo dye moiety and
$X^1$ is a ballasting group of sufficient size to render said BEND compound immobile and nondiffusible in the alkali-permeable layers of a photographic element.

27. A film unit of claim 26 wherein Q is an amino group, E is a carbonyl group and ENuP is a nitro group.

28. A film unit of claims 20, 21, 23, 24, 25, 26, or 27 wherein said electron transfer agent is a 3-pyrazolidone compound.

29. A film unit of claim 28 wherein the electron donor precursor has the structural formula:

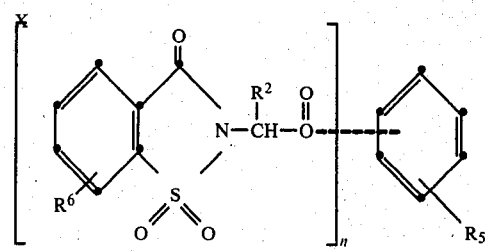

wherein:
n is 1;
$R^2$ is hydrogen or alkyl of 1 to 4 carbon atoms;
$R^5$ is hydrogen, halogen, nitro, alkyl of 1 to 30 carbon atoms, phenyl, acyl, ester or amido, provided that if $R^5$ is sulfonamido, carbonamido or phosphoramido it is in the ortho or meta position; and
$R^6$ is hydrogen, acyl, ester or amido.

30. A film unit of claim 29 wherein said electron donor precursor has a polarographic halfwave potential in 0.1 N sodium hydroxide more negative than −300 mV with respect to a saturated calomel electrode.

31. A film unit of claim 29 wherein the electron donor precursor has a polarographic halfwave potential in 0.1 N sodium hydroxide of between −360 and −600 mV.

32. In a process of forming an image with a photographic element containing exposed silver halide having associated therewith an immobile compound which upon reduction under alkaline conditions releases a diffusible dye or photographic reagent, said process comprising contacting said element with an alkaline processing composition in the presence of an electron transfer agent and an electron donor precursor to develop said exposed silver halide and to reduce said immobile compound as an inverse function of silver halide development and thereby release diffusible dye or photographic reagent, the improvement wherein said electron donor precursor has the structural formula:

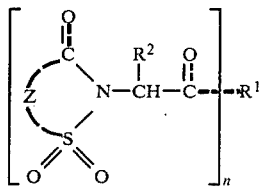

wherein:

Z represents the atoms to complete a bi- or tricyclic ring system, each ring of which contains 5 to 6 nuclear atoms;

n is 1 or 2;

$R^1$ is a monovalent aromatic group when n is 1 and a bivalent aromatic group when n is 2; and $R^2$ represents hydrogen, an alkyl group, an aryl group, an acyl group, an ester group or an amido group.

33. A process of claim 32 wherein Z is vinylene, phenylene or naphthylene which is unsubstituted or substituted with one or more halogen, amino, nitro, cyano, alkyl of 1 to 30 carbon atoms, alkoxy of 1 to 30 carbon atoms, aryl of 6 to 30 carbon atoms, aryloxy of 6 to 30 carbon atoms, acyl, ester or amido groups;

$R^1$ is phenyl, phenylene, biphenylyl, biphenylylene, naphthyl, naphthylene, anthryl or anthrylene which is unsubstituted or substituted with halogen, nitro, amino, cyano, alkyl of 1 to 30 carbon atoms, alkoxy of 1 to 30 carbon atoms, aryl of 6 to 30 carbon atoms, aryloxy of 6 to 30 carbon atoms, acyl, ester or amido, provided that sulfonamido, carbonamido or phosphoramido substituents are not in the 4-position of the aromatic group; and $R^2$ is hydrogen, alkyl of 1 to 30 carbon atoms, aryl of 6 to 30 carbon atoms, acyl, ester or amido.

34. A process of claim 32 wherein the electron donor precursor comprises a compound represented by the structural formula:

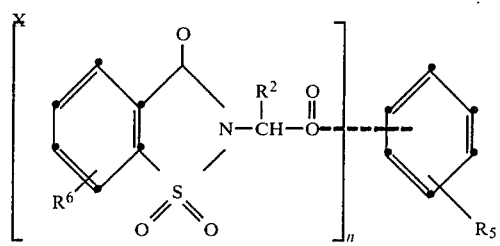

wherein:

n is 1 or 2;

$R^6$ is hydrogen, halogen, amino, nitro, cyano, alkyl of 1 to 30 carbon atoms, alkoxy of 1 to 30 carbon atoms, aryl of 6 to 30 carbon atoms, aryloxy of 6 to 30 carbon atoms, acyl, ester or amido;

$R^5$ is hydrogen, halogen, nitro, amino, cyano, alkyl of 1 to 30 carbon atoms, alkoxy of 1 to 30 carbon atoms, aryl of 6 to 30 carbon atoms, aryloxy of 6 to 30 carbon atoms, acyl, ester or amido, provided that sulfonamido, carbonamido or phosphoramido substituents are not in the 4-position of the aromatic group; and $R^2$ is hydrogen, alkyl of 1 to 30 carbon atoms, aryl of 6 to 30 carbon atoms, acyl, ester or amido.

35. A process of claim 34 wherein n is 1;

$R^2$ is hydrogen or alkyl of 1 to 4 carbon atoms;

$R^5$ is hydrogen, halogen, nitro, alkyl of 1 to 30 carbon atoms, phenyl, acyl, ester or amido, provided that if $R^5$ is sulfonamido, carbonamido or phosphoramido it is in the ortho or meta position; and $R^6$ is hydrogen, acyl ester or amido.

36. A process of claim 32 wherein said immobile compound releases diffusible dye as an inverse function of silver halide development and a viewable dye image is formed from at least one of said diffusible dye and said immobile compound.

37. A process of claim 36 wherein said diffusible dye is diffused to an image receiving layer where it forms a viewable image.

* * * * *